(12) United States Patent
Romanov et al.

(10) Patent No.: US 8,754,244 B1
(45) Date of Patent: Jun. 17, 2014

(54) RHODAMINE COMPOUNDS AND THEIR USE AS FLUORESCENT LABELS

(71) Applicant: Illumina Cambridge Limited, Essex (GB)

(72) Inventors: Nikolai Nikolaevich Romanov, Essex (GB); Xiaohai Liu, Essex (GB)

(73) Assignee: Illumina Cambridge Limited, Nr Saffron Walden (GB)

( * ) Notice: Subject to any disclaimer, the term of this patent is extended or adjusted under 35 U.S.C. 154(b) by 0 days.

(21) Appl. No.: 13/790,776

(22) Filed: Mar. 8, 2013

Related U.S. Application Data

(60) Provisional application No. 61/774,898, filed on Mar. 8, 2013.

(51) Int. Cl.
*C07D 311/78* (2006.01)

(52) U.S. Cl.
USPC ........... 549/394; 549/356; 549/381; 549/388; 436/800

(58) Field of Classification Search
USPC ................... 549/356, 381, 385, 394; 436/800
See application file for complete search history.

(56) References Cited

U.S. PATENT DOCUMENTS

| 6,399,392 B1 * | 6/2002 | Haugland et al. ............. 436/172 |
| 6,750,357 B1 * | 6/2004 | Chiarello et al. ............. 549/394 |
| 8,178,360 B2 | 5/2012 | Barnes et al. |
| 8,445,702 B2 * | 5/2013 | Gee ................................. 549/225 |
| 2006/0160081 A1 | 7/2006 | Milton et al. |
| 2009/0227467 A1 | 9/2009 | Chang et al. |

FOREIGN PATENT DOCUMENTS

| CN | 102645844 | 8/2012 |
| JP | 01113497 | 5/1989 |
| JP | 01113500 | 5/1989 |
| JP | 09241558 | 9/1997 |
| WO | 2004/018493 | 3/2004 |
| WO | 2007020457 | 2/2007 |
| WO | 2007/135368 | 11/2007 |
| WO | 2009051807 | 4/2009 |
| WO | 2009054922 | 4/2009 |
| WO | WO 2010/033011 | 3/2010 |

OTHER PUBLICATIONS

Guo, J. et al., "Four-color DNA sequencing with 3'-O-modified nucleotide reversible terminators and chemically cleavable fluorescent dideoxynucleotides", PNAS, 105(27), 2008, 9145-9150.
Qiu, Chunmei et al., "Design and synthesis of cleavable biotinylated dideoxynucleotides for DNA sequencing by matrix-assisted laser desorption/ionization time-of-flight mass spectrometry", Analytical Biochemistry 427, 2012, 193-201.
Buchynskyy, et al., "Synthesis of fluorescent derivatives of the antibiotic moenomycin A", European Journal of Organic Chemistry, No. 7, Dewiley-VCH, Weinheim.ISSN: 1434-193X, 2002, 1149-1162.
International Search Report, "Application No. PCT/EP2013/054793", mailed Nov. 28, 2013.

* cited by examiner

*Primary Examiner* — Golam M M Shameem
(74) *Attorney, Agent, or Firm* — Brent C. Moore; Illumina, Inc.

(57) ABSTRACT

The present invention relates to new rhodamine compounds and their use as fluorescent labels. The compounds may be used as fluorescent labels for nucleotides in nucleic acid sequencing applications.

12 Claims, 4 Drawing Sheets

RHODAMINE COMPOUNDS AND THEIR USE AS FLUORESCENT LABELS

RELATED APPLICATIONS

This application claims priority to U.S. Provisional Application No. 61/774,898, filed on Mar. 8, 2013, which is hereby incorporated by reference in its entirety.

The present invention relates to new rhodamine compounds and their use as fluorescent labels. The compounds may be used as fluorescent labels, particularly for nucleotide labelling in nucleic acid sequencing applications.

BACKGROUND

Several publications and patent documents are referenced in this application in order to more fully describe the state of the art to which this invention pertains. The disclosure of each of these publications and documents is incorporated by reference herein.

Non-radioactive detection of nucleic acids utilizing fluorescent labels is an important technology in molecular biology. Many procedures employed in recombinant DNA technology previously relied heavily on the use of nucleotides or polynucleotides radioactively labelled with, for example $^{32}$P. Radioactive compounds permit sensitive detection of nucleic acids and other molecules of interest. However, there are serious limitations in the use of radioactive isotopes such as their expense, limited shelf life and more importantly safety considerations. Eliminating the need for radioactive labels enhances safety whilst reducing the environmental impact and costs associated with, for example, reagent disposal. Methods amenable to non-radioactive fluorescent detection include by way of non-limiting example, automated DNA sequencing, hybridization methods, real-time detection of polymerase-chain-reaction products and immunoassays.

For many applications it is desirable to employ multiple spectrally distinguishable fluorescent labels in order to achieve independent detection of a plurality of spatially overlapping analytes. In such multiplex methods the number of reaction vessels may be reduced simplifying experimental protocols and facilitating the production of application-specific reagent kits. In multi-colour automated DNA sequencing for example, multiplex fluorescent detection allows for the analysis of multiple nucleotide bases in a single electrophoresis lane thereby increasing throughput over single-colour methods and reducing uncertainties associated with inter-lane electrophoretic mobility variations.

However, multiplex fluorescent detection can be problematic and there are a number of important factors which constrain selection of fluorescent labels. First, it is difficult to find dye compounds whose emission spectra are suitably spectrally resolved. In addition when several fluorescent dyes are used together, simultaneous excitation may be difficult because the absorption bands of the dyes are usually widely separated. Many excitation methods use high power lasers and therefore the dye must have sufficient photo-stability to withstand such laser excitation. A final consideration of particular importance in molecular biology methods is that the fluorescent dyes must be compatible with the reagent chemistries used such as for example DNA synthesis solvents and reagents, buffers, polymerase enzymes and ligase enzymes.

As sequencing technology advances a need has developed for further fluorescent dye compounds, their nucleic acid conjugates and dye sets which satisfy all of the above constraints and which are amenable particularly to high throughput molecular methods such as solid phase sequencing and the like.

Application WO2007135368 describes a class of rhodamine compounds suitable for use as fluorescent labels. The compounds described therein are suitable for use in solid phase nucleic acid sequencing protocols. Advances in the technology and throughput of solid phase nucleic acid sequencing have led to further developments and improvements to the molecular design of fluorescent labels, particularly in the context of the interaction between the fluorescent reagents and particular nucleic acid sequences.

Fluorescent dye molecules with improved fluorescence properties (such as fluorescence intensity, position of fluorescence maximum and shape of fluorescence band) can improve the speed and accuracy of nucleic acid sequencing. Fluorescence signal intensity is especially important when measurements are made in water based biological buffers and/or at higher temperature as fluorescence of most dyes is significantly lower at such conditions. Moreover, the nature of the base to which a dye is attached also affects the fluorescence maximum, fluorescence intensity and other spectral dye properties. The sequence specific interactions between the fluorescent dye and the nucleobase can be tailored by specific design of the fluorescent dyes. Optimisation of the structure of the fluorescent dyes can improve their fluorescent properties and also improve the efficiency of nucleotide incorporation, reduce the level of sequencing errors and decrease the usage of reagents in, and therefore the costs of, nucleic acid sequencing.

Described herein are improved rhodamine constructs and their use as bio-molecule labels, particularly as labels for nucleotides used in nucleic acid sequencing. The improvements can be seen in the higher fluorescence intensities of such dyes when prepared as bio-molecule conjugates and in the length and quality of sequencing read obtainable using the new fluorescent constructs.

SUMMARY

According to a first aspect the invention provides rhodamine dye compounds of the formula (I) and mesomers thereof:

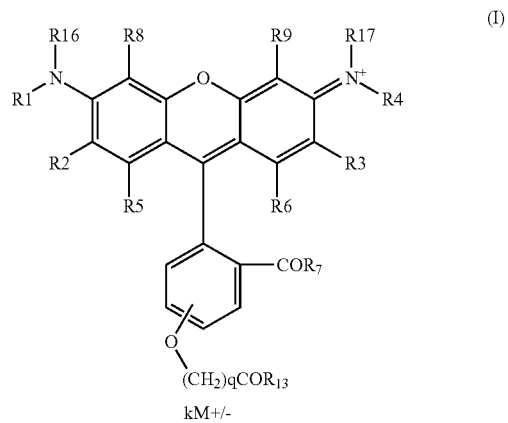

Mesomers of the invention may include formula's represented by 1a, 1b or cyclic form 1c:

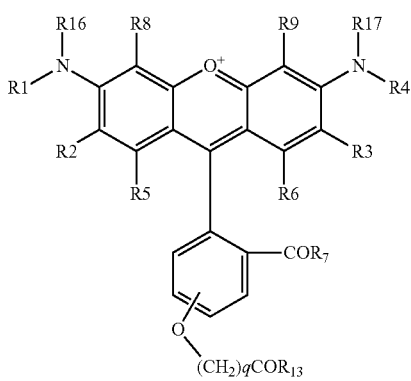
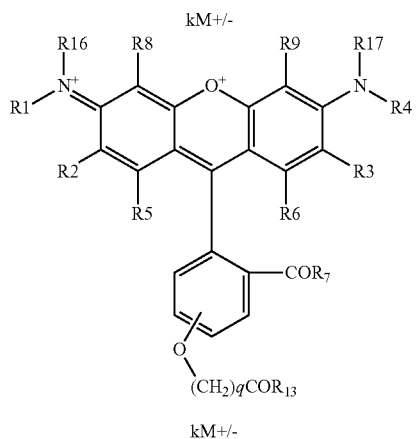
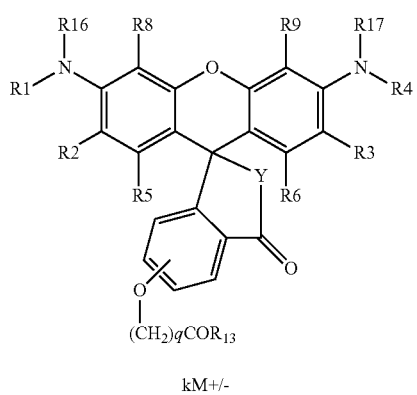

In formula's I, Ia, Ib or Ic,
$M^{+/-}$ is a common counter ion,
k is an integer of from 0 to 6,
q is an integer of from 1 to 6,
$Y=O, NR_{11}$,
$R_1$ is H or an alkyl, aryl or substituted alkyl or substituted aryl group,
$R_2$ is H, alkyl or substituted alkyl group, halogen, carboxy, carboxamide, hydroxy- or alkoxy group, or $R_2$ together with $R_1$ or $R_5$ is a carbon or heterosubstituted chain forming a ring,
$R_3$ is H, alkyl or substituted alkyl group, halogen, carboxy, carboxamide, hydroxy- or alkoxy group or $R_3$ together with $R_4$ or $R_6$ is a carbon or heterosubstituted chain forming a ring,
$R_4$ is H or an alkyl, aryl or substituted alkyl or substituted aryl group,
$R_5$ and $R_6$ are H, alkyl or substituted alkyl group, halogen, hydroxy- or alkoxy group, $R_8$ is H, halogen, hydroxy- or alkoxy group, alkyl or substituted alkyl group or together with $R_1$ is a carbon or heterosubstituted carbon chain forming a ring,
$R_9$ is H, halogen, hydroxy- or alkoxy group, alkyl or substituted alkyl group or together with $R_4$ is a carbon or heterosubstituted carbon chain forming a ring,
$R_7$ is $OR_{11}$ or $NR_{11}R_{12}$ where $R_{11}$ and $R_{12}$ are independently H, alkyl or a substituted alkyl,
$R_{13}$ is $OR_{14}$ or $NR_{14}R_{15}$ where $R_{14}$ and $R_{15}$ are independently H, alkyl or a substituted alkyl; aryl or a substituted aryl, and
$R_{16}$ and $R_{17}$ are independently H or an alkyl, aryl or substituted alkyl or substituted aryl group.

In another embodiment the compounds of the present invention can be conjugated with a variety of substrate moieties such as, for example, nucleosides, nucleotides, polynucleotides, polypeptides, carbohydrates, ligands, particles and surfaces.

According to a further aspect of the invention therefore, there are provided dye compounds comprising linker groups to enable, for example, covalent attachment to such substrate moieties.

According to a further aspect the invention provides a nucleoside or nucleotide compound defined by the formula: N-L-Dye, wherein N is a nucleotide, L is an optional linker moiety and Dye is a fluorescent compound according to the present invention.

In a further aspect the invention includes methods of sequencing using the dye compounds of the present invention.

According to a further aspect the invention also provides kits comprising dye compounds of the invention (free or in conjugate form) which may be used in various immunological assays, oligonucleotide and nucleic acid labelling and for DNA sequencing by synthesis. In yet another aspect the invention provides kits comprising dye 'sets' particularly suited to cycles of sequencing by synthesis on an automated instrument platform.

A further aspect of the invention is the chemical preparation of compounds of the invention.

DESCRIPTION OF FIGURES

FIG. 1 shows the relative intensity of the dyes at each temperature. The commercial dye Atto532 shows a greater loss of fluorescence intensity at higher temperatures relative to the I-1 and I-3 dyes. FIG. 1 demonstrates that the fluorescence of the new dyes in water based solutions is less variable with the temperature.

FIG. 4 shows a plot of red intensity vs green intensity in an Illumina 4 colour sequencing run. The higher distance between the groups of dyes signals lowers the chances of a miss-call, and therefore increases the accuracy of sequencing. The increase in brightness of the I-3 dye compared to the commercial dye means the sequencing data is improved.

DETAILED DESCRIPTION

Figure 1:
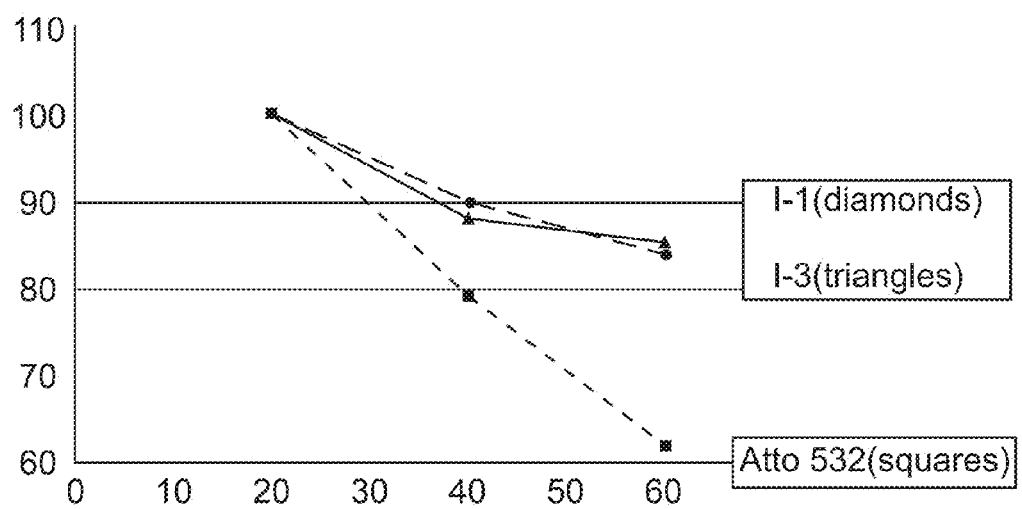
FIG. 1 shows the lower temperature decrease of the dyes as described herein compared to prior art dyes. Normalized fluorescence intensities of $1.10^{-6}$ M solutions of dyes (I-1) and (I-3) were compared with commercially available dye Atto532 for the same spectral region at different temperature. The intensity of the dyes at 20, 40 and 60° C. were measured.

The invention relates to novel rhodamine dye compounds particularly suitable for methods of fluorescence detection and sequencing by synthesis.

According to a first aspect the invention provides rhodamine dye compounds of the formula (I):

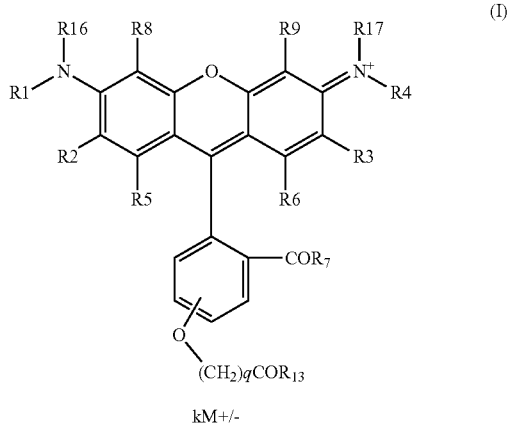

(I)

wherein
$M^{+/-}$ is a common counter ion,
k is an integer of from 0 to 6,
q is an integer of from 1 to 6,
$R_1$ is H or an alkyl, aryl or substituted alkyl or substituted aryl group,
$R_2$ is H, alkyl or substituted alkyl group, halogen, carboxy, carboxamide, hydroxy- or alkoxy group, or $R_2$ together with $R_1$ or $R_5$ is a carbon or hetero-substituted chain forming a ring,
$R_3$ is H, alkyl or substituted alkyl group, halogen, carboxy, carboxamide, hydroxy- or alkoxy group or $R_3$ together with $R_4$ or $R_6$ is a carbon or hetero-substituted chain forming a ring,
$R_4$ is H or an alkyl, aryl or substituted alkyl or substituted aryl group,
$R_5$ and $R_6$ are H, alkyl or substituted alkyl group, halogen, hydroxy- or alkoxy group,
$R_8$ is H, halogen, hydroxy- or alkoxy group, alkyl or substituted alkyl group or together with $R_1$ is a carbon or hetero-substituted carbon chain forming a ring,
$R_9$ is H, halogen, hydroxy- or alkoxy group, alkyl or substituted alkyl group or together with $R_4$ is a carbon or hetero-substituted carbon chain forming a ring, $R_7$ is $OR_{11}$ or $NR_{11}R_{12}$ where $R_{11}$ and $R_{12}$ are independently H, alkyl or a substituted alkyl,
$R_{13}$ is $OR_{14}$ or $NR_{14}R_{15}$ where $R_{14}$ and $R_{15}$ are independently H, alkyl or a substituted alkyl; aryl or a substituted aryl, and
$R_{16}$ and $R_{17}$ are independently H or an alkyl, aryl or substituted alkyl or substituted aryl group.

$R_{16}$ and $R_{17}$ can be independently H or an alkyl, aryl or substituted alkyl or substituted aryl group. The alkyl group can be substituted with $SO_3^-$. Where $R_{16}$ or $R_{17}$ is an alkyl substituted with $SO_3^-$, the $SO_3^-$ group may be coordinated with a counter ion, for example metal ions or ammonium ions. $R_{16}$ and $R_{17}$ can be H. Compounds of the invention therefore include compounds of formula (II) and mesomers thereof:

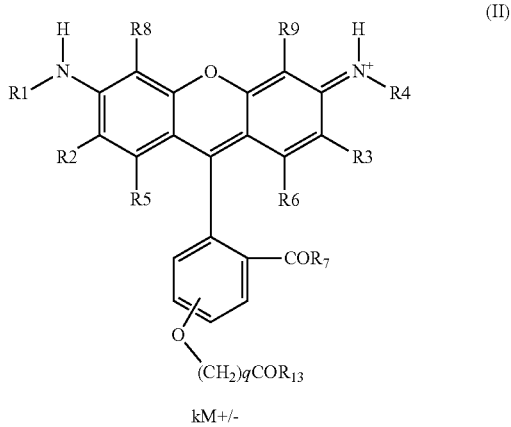

(II)

wherein $M^{+/-}$ is a common counter ion,
k is an integer of from 0 to 6,
q is an integer of from 1 to 6,
$R_1$ is H or an alkyl, aryl or substituted alkyl or substituted aryl group,
$R_2$ is H, alkyl or substituted alkyl group, halogen, carboxy, carboxamide, hydroxy- or alkoxy group, or $R_2$ together with $R_1$ or $R_5$ is a carbon or hetero-substituted chain forming a ring,
$R_3$ is H, alkyl or substituted alkyl group, halogen, carboxy, carboxamide, hydroxy- or alkoxy group or $R_3$ together with $R_4$ or $R_6$ is a carbon or hetero-substituted chain forming a ring,
$R_4$ is H or an alkyl, aryl or substituted alkyl or substituted aryl group,
$R_5$ and $R_6$ are H, alkyl or substituted alkyl group, halogen, hydroxy- or alkoxy group,
$R_8$ is H, halogen, hydroxy- or alkoxy group, alkyl or substituted alkyl group or together with $R_1$ is a carbon or hetero-substituted carbon chain forming a ring,
$R_9$ is H, halogen, hydroxy- or alkoxy group, alkyl or substituted alkyl group or together with $R_4$ is a carbon or hetero-substituted carbon chain forming a ring,
$R_7$ is $OR_{11}$ or $NR_{11}R_{12}$ where $R_{11}$ and $R_{12}$ are independently H, alkyl or a substituted alkyl, and
$R_{13}$ is $OR_{14}$ or $NR_{14}R_{15}$ where $R_{14}$ and $R_{15}$ are independently H, alkyl or a substituted alkyl; aryl or a substituted aryl.

Where $R_{16}$ and/or $R_{17}$ is unsubstituted alkyl —$(CH_2)_nH$ or —$(CH_2)_mH$, n and m may be 1-6. Compounds of the invention therefore include compounds of formula (IIa):

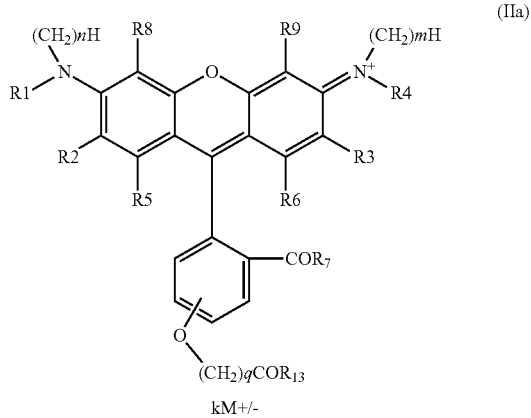

(IIa)

wherein M⁻ is a common counter ion, k, n, and m are independently integers of from 0 to 6, q is an integer of from 1 to 6, $R_1$ is H or an alkyl, aryl or substituted alkyl or substituted aryl group, $R_2$ is H, alkyl or substituted alkyl group, halogen, carboxy, carboxamide, hydroxy- or alkoxy group, or $R_2$ together with $R_1$ or $R_5$ is a carbon or heterosubstituted chain forming a ring, $R_3$ is H, alkyl or substituted alkyl group, halogen, carboxy, carboxamide, hydroxy- or alkoxy group or $R_3$ together with $R_4$ or $R_6$ is a carbon or heterosubstituted chain forming a ring, $R_4$ is H or an alkyl, aryl or substituted alkyl or substituted aryl group, $R_5$ and $R_6$ are H, alkyl or substituted alkyl group, halogen, hydroxy- or alkoxy group, $R_8$ is H, halogen, hydroxy- or alkoxy group, alkyl or substituted alkyl group or together with $R_1$ is a carbon or heterosubstituted carbon chain forming a ring, $R_9$ is H, halogen, hydroxy- or alkoxy group, alkyl or substituted alkyl group or together with $R_4$ is a carbon or heterosubstituted carbon chain forming a ring, $R_7$ is $OR_{11}$ or $NR_{11}R_{12}$ where $R_{11}$ and $R_{12}$ are independently H, alkyl or a substituted alkyl, and $R_{13}$ is $OR_{14}$ or $NR_{14}R_{15}$ where $R_{14}$ and $R_{15}$ are independently H, alkyl or a substituted alkyl; aryl or a substituted aryl.

n and m may be the same or different. n may be 1, 2, 3, 4, 5 or 6. m may be 1, 2, 3, 4, 5 or 6. The —(CH₂)n—H or —(CH₂)m—H may be C1-6 alkyl groups, for example methyl, ethyl or propyl, and may be optionally substituted.

q may be 1, 2, 3, 4, 5 or 6. In addition to the $(CH_2)_q$ linker, the linker may contain substituents at any carbon atoms or additional heteroatoms. For example the linker may contain additional oxygen atoms in the form of ethylene glycol type spacers —(CH₂CH₂O)ₙ—. The linker is present to attach the biomolecule through $COR_{13}$ residue in form of an acid, ester or amide group to the rest of the construct responsible for fluorescence and to separate the biomolecule from the dye molecule.

$R_1$ may be H or an alkyl or substituted alkyl group. $R_1$ can be chosen such that $R_1$ may not be H when n is zero. $R_1$ can be methyl or ethyl. $R_1$ can be linked to $R_2$ and/or $R_8$ to form a ring structure. The ring may be a 5 or 6 membered ring. The ring may be an all carbon ring, or may contain additional heteroatoms.

$R_2$ may be H, alkyl or substituted alkyl group, halogen, carboxy, carboxamide, hydroxy- or alkoxy group. Optionally, $R_2$ together with $R_1$ or $R_5$ is a carbon or heterosubstituted chain forming a ring.

$R_3$ may be H, alkyl or substituted alkyl group, halogen, carboxy, carboxamide, hydroxy or alkoxy group. Optionally $R_3$ together with $R_4$ or $R_6$ is a carbon or hetero-substituted chain forming a ring.

$R_4$ may be H or an alkyl or substituted alkyl group. $R_4$ is not H when m is zero. $R_4$ can be methyl or ethyl. $R_4$ can be linked to $R_3$ and/or $R_9$ to form a ring structure. The ring may be a 5 or 6 membered ring. The ring may be an all carbon ring, or may contain additional heteroatoms.

$R_5$ and $R_6$ may be H, alkyl or substituted alkyl group, halogen, hydroxy or alkoxy group. Optionally $R_5$ may be linked to $R_2$, and $R_6$ may be linked to $R_3$.

$R_8$ may be H, halogen, hydroxy or alkoxy group, alkyl or substituted alkyl group. Optionally $R_8$ may be linked together with $R_1$ to form a carbon or heterosubstituted carbon chain forming a ring.

$R_9$ may be H, halogen, hydroxy or alkoxy group, alkyl or substituted alkyl group. Optionally $R_9$ may be linked together with $R_4$ to form a carbon or heterosubstituted carbon chain forming a ring.

$R_7$ together with the C=O forms an acid, ester or amide group. In particular $R_7$ may be $OR_{11}$ or $NR_{11}R_{12}$ where $R_{11}$ and $R_{12}$ are independently H, alkyl or a substituted alkyl, aryl or a substituted aryl. When $R_{11}$ and $R_{12}$ are H $R_7$ may be OH or $NH_2$. $R_7$ may be an alkoxy group or a primary or secondary amine group with one or two alkyl and/or aryl groups. The ester or amide $COR_7$ may be further optionally substituted.

$R_{13}$ together with the C=O is forms an acid, ester or amide group. In particular $R_{13}$ may be $OR_{14}$ or $NR_{14}R_{15}$ where $R_{14}$ and $R_{15}$ are independently H, alkyl or a substituted alkyl, aryl or substituted aryl. $R_{13}$ may be OH or $NH_2$. $R_{13}$ may be an alkoxy or a primary or secondary amine with one or two alkyl/aryl groups. The ester or amide may be further optionally substituted. $R_{13}$ may be $NR_{14}R_{15}$ where $R_{14}$ is H or alkyl and $R_{15}$ is alkyl or a substituted alkyl. The substitution may allow the conjugation to biomolecules. The molecules may be attached to rhodamine dye core structural fragment through $R_{13}$ for further use.

Compounds of the invention may include the compound where $R_{16}$ and $R_{17}$ are unsubstituted alkyl —(CH₂)ₙH and —(CH₂)ₘH where n is 1-3, $R_1$, $R_4$, $R_5$, $R_6$, $R_8$ and $R_9$ are all H, $R_2$ and $R_3$ are H or $CH_3$. Such compounds are shown in formula (III) below:

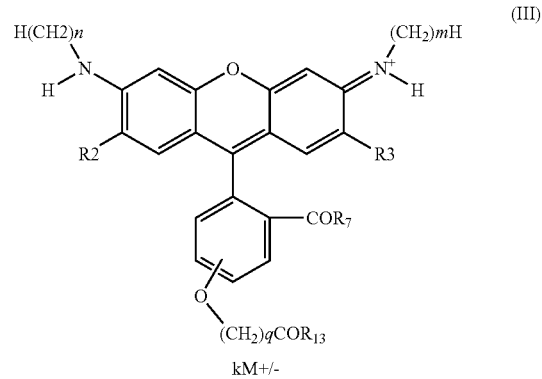

(III)

where k, n, m are independently integers of from 1 to 3, q is an integer of from 1 to 6, $R_2$ and $R_3$ are independently H or $CH_3$, $R_7$ is $OR_{11}$ or $NR_{11}R_{12}$ where $R_{11}$ and $R_{12}$ are independently H, alkyl or a substituted alkyl, and $R_{13}$ is $OR_{14}$ or $NR_{14}R_{15}$ where $R_{14}$ and $R_{15}$ are independently H, alkyl or a substituted alkyl; aryl or a substituted aryl.

Compounds of the invention may include the compound where $R_{16}$ and $R_{17}$ are H, $R_1$ is linked to $R_2$ or $R_8$ via a chain of $CH_2$ groups to form a ring, and $R_4$ is linked to $R_3$ or $R_9$ via a chain of $CH_2$ groups to form a ring.

Compounds of the invention may include the compound where $R_{16}$ and $R_{17}$ are H, $R_1$ is linked to $R_2$ via a chain of $CH_2$ groups to form a 6 membered ring, and $R_4$ is linked to $R_3$ via a chain of $CH_2$ groups to form a 6 membered ring. Such compounds are shown in formula (IV) below:

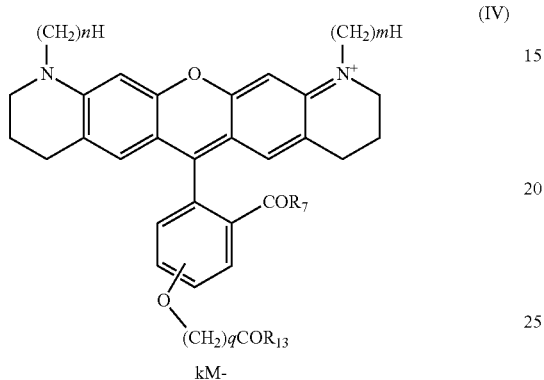

(IV)

kMwhere k, n, m are independently integers of from 1 to 3, where q is an integer of from 1 to 6, $R_7$ is $OR_{11}$ or $NR_{11}R_{12}$ where $R_{11}$ and $R_{12}$ are independently H, alkyl or a substituted alkyl, and $R_{13}$ is $OR_{14}$ or $NR_{14}R_{15}$ where $R_{14}$ and $R_{15}$ are independently H, alkyl or a substituted alkyl; aryl or a substituted aryl.

Dyes of the invention may include the compounds where any of $R_1$, $R_4$, $R_{16}$ or $R_{17}$ are H or alkyl. The alkyl may be substituted with $SO_3^-$ Compounds of the invention may include the compound where $R_1$ and $R_4$ are H and $R_{16}$ and/or $R_{17}$ is $SO_3^-$.

The $R_{13}CO-(CH_2)_q-$ group is joined to rhodamine dye core structural fragment via a heteroatom, for example an oxygen atom. This heteroatom, may be attached to any of carbon atoms of the phenyl ring of the rhodamine dye core structural fragment. The compounds may be prepared and used as mixtures of positional isomers where the heteroatom or oxygen atom is present at different positions of the benzene ring, or the compounds may be prepared and used as single isomers. Optionally the benzene ring of such new rhodamine dyes may contain additional substituents for further fine tuning of their spectral parameters.

Compounds of the invention include compounds according to formula (Va) and (Vb), and mixtures thereof:

(Va)

kM+/-

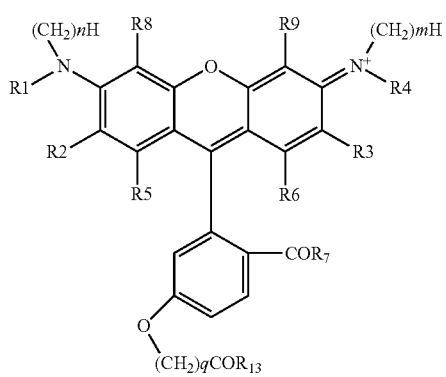

-continued (Vb)

kM+/-

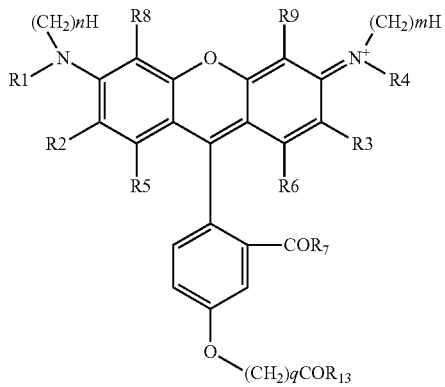

wherein $M^{+/-}$ is a common counter ion, k is an integer of from 0 to 6, q is an integer of from 1 to 6, $R_1$ is H or an alkyl, aryl or substituted alkyl or substituted aryl group, $R_2$ is H, alkyl or substituted alkyl group, halogen, carboxy, carboxamide, hydroxy- or alkoxy group, or $R_2$ together with $R_1$ or $R_5$ is a carbon or heterosubstituted chain forming a ring, $R_3$ is H, alkyl or substituted alkyl group, halogen, carboxy, carboxamide, hydroxy- or alkoxy group or $R_3$ together with $R_4$ or $R_6$ is a carbon or heterosubstituted chain forming a ring, $R_4$ is H or an alkyl, aryl or substituted alkyl or substituted aryl group, $R_5$ and $R_6$ are H, alkyl or substituted alkyl group, halogen, hydroxy- or alkoxy group, $R_8$ is H, halogen, hydroxy- or alkoxy group, alkyl or substituted alkyl group or together with $R_1$ is a carbon or heterosubstituted carbon chain forming a ring, $R_9$ is H, halogen, hydroxy- or alkoxy group, alkyl or substituted alkyl group or together with $R_4$ is a carbon or heterosubstituted carbon chain forming a ring, $R_7$ is $OR_{11}$ or $NR_{11}R_{12}$ where $R_{11}$ and $R_{12}$ are independently H, alkyl or a substituted alkyl, $R_{13}$ is $OR_{14}$ or $NR_{14}R_{15}$ where $R_{14}$ and $R_{15}$ are independently H, alkyl or a substituted alkyl; aryl or a substituted aryl, and $R_{16}$ and $R_{17}$ are independently H or an alkyl, aryl or substituted alkyl or substituted aryl group.

The compounds of the invention may be attached to biomolecules. The compounds of the invention may be attached to oligonucleotides. The compounds of the invention may be attached to nucleotides. The compounds may be attached to oligonucleotides or nucleotides via the nucleotide base.

The attachment to the biomolecules may be via one of $COR_7$ and/or $R_{13}CO(CH2)q-O-$ group or via both of these. The $R_7$ and/or $R_{13}$ group may be an alkyl-, aryl-, or heteryloxy groups, primary or secondary amine with a substituted group $R_{15}$, which may be used for attachment. In particular one of $COR_7$ and/or $R_{13}CO(CH2)q-O-$ group may be activated ester residue most suitable for further amide/peptide bond formation.

For example, $R_7$ and/or $R_{13}$ may be:

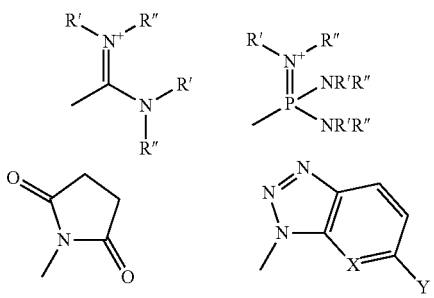

Examples of compounds of the invention include:

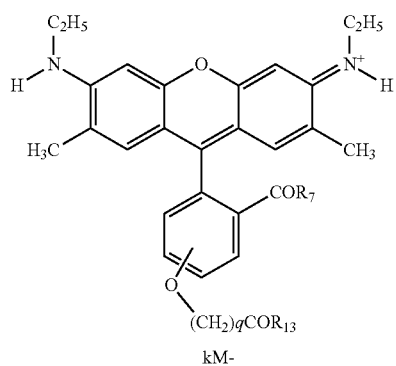

and

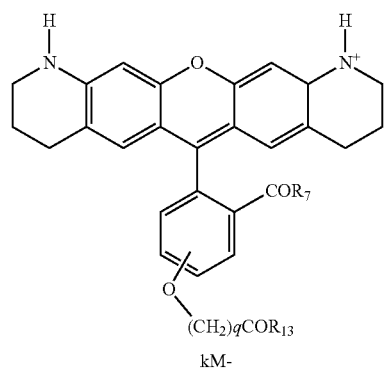

where q is an integer of from 1 to 6,
$R_7$ is $OR_{11}$ or $NR_{11}R_{12}$ where $R_{11}$ and $R_{12}$ are independently H, alkyl or a substituted alkyl, and
$R_{13}$ is $OR_{14}$ or $NR_{14}R_{15}$ where $R_{14}$ and $R_{15}$ are independently H, alkyl or a substituted alkyl; aryl or a substituted aryl.

Further examples include

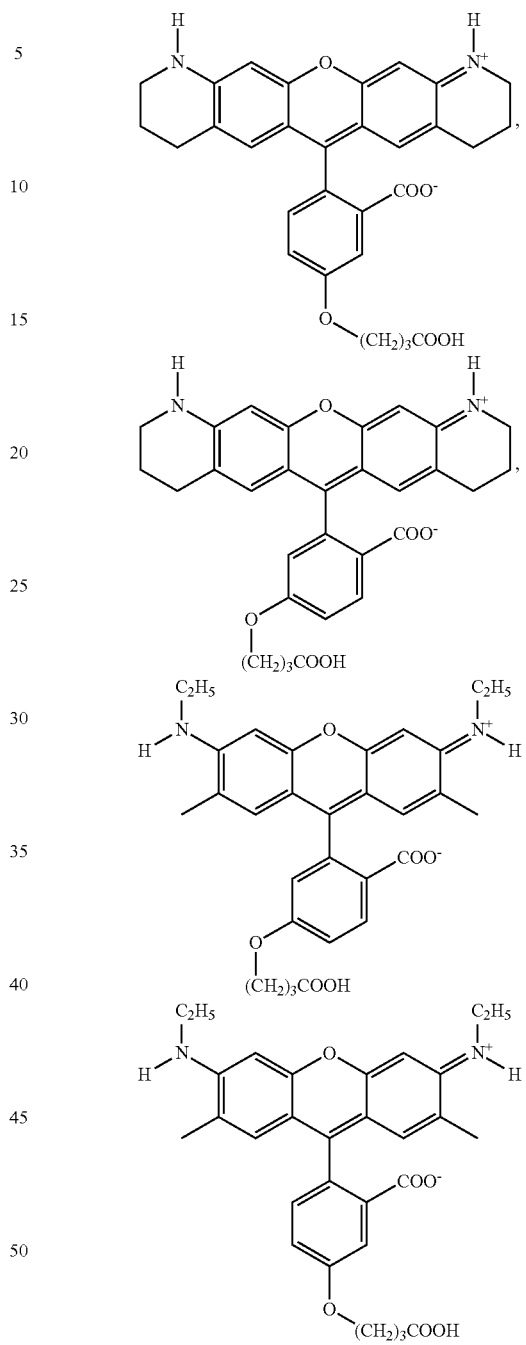

An aspect of the invention is a nucleotide or oligonucleotide labelled with a fluorescent compound as described herein. The labelled nucleotide or oligonucleotide may have the label attached via substituted alkyl group $R_{15}$. The labelled nucleotide or oligonucleotide may have the label attached to the C5 position of a pyrimidine base or the C7 position of a 7-deaza purine base through a linker moiety.

The labelled nucleotide or oligonucleotide may also have a 3' OH blocking group covalently attached to the ribose or deoxyribose sugar of the nucleotide.

Disclosed herein are kits comprising two or more nucleotides wherein at least one nucleotide is a nucleotide labelled with a compound of the present invention. The kit may comprise two or more labelled nucleotides. The nucleotides may be labelled with two or more fluorescent labels. Two or more of the labels may be excited using a single excitation source, which may be a laser.

The kit may contain four labelled nucleotides, where the first of four nucleotides is labelled with a compound as disclosed herein, and the second, third, and fourth nucleotides are each labelled with a different compound, wherein each compound has a distinct absorbance maximum and each of the compounds is distinguishable from the other three compounds. The kit may be such that two or more of the compounds have a distinct absorbance maximum above 600 nm.

The compounds of the invention, nucleotides or kits may be used in sequencing, expression analysis, hybridisation analysis, genetic analysis, RNA analysis or protein binding assays. The use may be on an automated sequencing instrument. The sequencing instrument may contain two lasers operating at different wavelengths.

Disclosed herein is new compounds of formula (Xa,b) as starting materials for synthesising of dyes formula (I) in according with the invention.

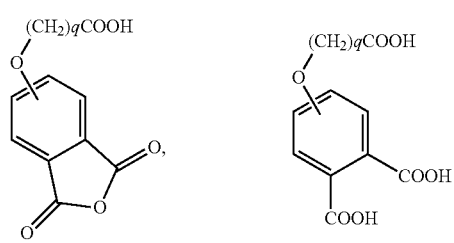

(Xa,b)

where q is 1-6.

Disclosed herein is a method of synthesising compounds of the invention. A compound of formula (Xa,b) may be used in a condensation reaction with a substituted or unsubstituted 3-amino phenol derivative or heterocyclic derivative which contains this structural fragment. Dyes of formula (I) have been synthesized by a condensation of the phthalic acid derivatives (Xa,b) with 3-amino-phenol derivatives, preferably at high temperature, with or without Lewis acid catalysts. Reaction could be fulfilled also by using phosphoric or poly-phosphoric acids as solvent and/or a catalyst. Condensation reaction may be accomplished with or without catalysts in ionic liquids or high-boiling point polar organic solvent like DMF, DMA, sulfolane or 1,2-dichlorobenzene.

As used herein, the term "alkyl" refers to C1-C20 hydrocarbon and may include C3-C10 non-aromatic carbocyclic rings. In particular embodiments the alkyl groups are C1-C6 alkyl which refers to saturated, straight- or branched-chain hydrocarbon radicals containing between one and six carbon atoms, respectively. Alkyl groups may include one or more unsaturated groups, and thus include alkenyl and alkynyl.

The term "halogen" as used herein refers to fluoro-(hereafter designated as F), chloro-(hereafter designated as Cl), bromo-(hereafter designated as Br) or iodo-(hereafter designated as I), and usually relates to substitution for a hydrogen atom in an organic compound, this substitution is optionally a full substitution for the hydrogen.

The term "substituted alkyl", refers to alkyl, alkenyl or alkynyl groups as defined above where they may optionally be further substituted with, but not limited to, halo, cyano, $SO_3^-$, SRa, ORa, NRbRc, oxo, CONRbRc, COOH and COORb. Ra, Rb and Rc may be each independently selected from H, alkyl, substituted alkyl, alkenyl, substituted alkenyl, alkynyl, substituted alkynyl, aryl and substituted aryl. Further, said substituted alkyl, substituted alkenyl and substituted alkynyl may optionally be interrupted by at least one hetero atom or group selected from O, NRb, S(O)$_t$ where t is 0 to 2, and the like. Substituted alkyl also covers group such as benzyl where the alkyl groups is comprises a further aryl or substituted aryl moiety.

Dyes according to the present invention may be synthesised from a variety of different starting materials, including N- and/or C-substituted derivatives of 3-aminophenol, 5-hydroxy- and/or 7-hydroxy-1,2,3,4-tetrahydroquinoline derivatives and other similar aromatic or heterocyclic starting materials which contain m-aminophenol structural fragment. Condensation of these compounds with additionally substituted or unsubstituted phthalic acid derivatives formula Xa,b gives the dyes as described. The condensation reaction is typically carried out at high temperature with or without suitable solvent, and is assisted by the use of microwave irradiation. The use of ionic liquids as solvent in said condensation reactions is especially advantageous. The reaction can be catalysed by Lewis acids.

Dyes according to the invention may be synthesised also by conventional alkylation methods starting from hydroxy-substituted rhodamine dyes formula (XI)

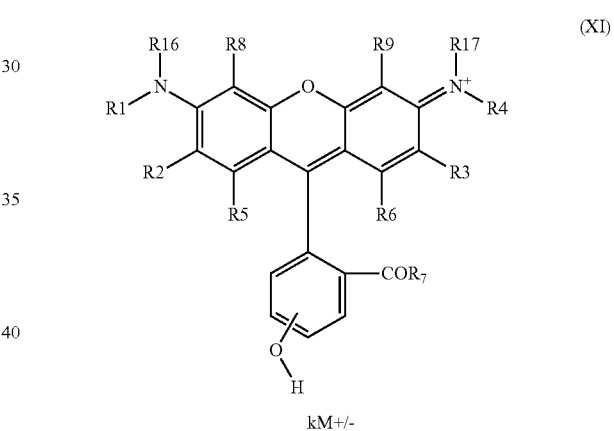

(XI)

$M^{+/-}$ is a common counter ion, k is an integer of from 0 to 6, $R_1$ is H or an alkyl, aryl or substituted alkyl or substituted aryl group, $R_2$ is H, alkyl or substituted alkyl group, halogen, carboxy, carboxamide, hydroxy- or alkoxy group, or $R_2$ together with $R_1$ or $R_5$ is a carbon or heterosubstituted chain forming a ring, $R_3$ is H, alkyl or substituted alkyl group, halogen, carboxy, carboxamide, hydroxy- or alkoxy group or $R_3$ together with $R_4$ or $R_6$ is a carbon or heterosubstituted chain forming a ring, $R_4$ is H or an alkyl, aryl or substituted alkyl or substituted aryl group, $R_5$ and $R_6$ are H, alkyl or substituted alkyl group, halogen, hydroxy- or alkoxy group, $R_8$ is H, halogen, hydroxy- or alkoxy group, alkyl or substituted alkyl group or together with $R_1$ is a carbon or heterosubstituted carbon chain forming a ring, $R_9$ is H, halogen, hydroxy- or alkoxy group, alkyl or substituted alkyl group or together with $R_4$ is a carbon or heterosubstituted carbon chain forming a ring, $R_7$ is $OR_{11}$ or $NR_{11}R_{12}$ where $R_{11}$ and $R_{12}$ are independently H, alkyl or a substituted alkyl, and R$_{16}$ and R$_{17}$ are independently H or an alkyl, aryl or substituted alkyl or substituted aryl group.

Dyes formula (XI) can be prepared by condensation of 3-aminophenol derivatives with hydroxyl-phthalic acid derivatives as described below.

Preparation of N-alkyl-5-hydroxy-1,2,3,4-tetrahydroquinoline or N-sulfonatoalkyl-7-hydroxy-1,2,3,4-tetrahydroquinoline can be carried out using chemical or catalytic hydrogenation, for example using Raney Nickel as a catalyst. The addition of an organic or inorganic base, for example triethylamine, greatly enhances the rate of reaction.

Mono N-alkylation of 3-aminophenols with alkylsultones can be carried out using one equivalent or more of the aminophenol. Di-alkylation of 3-amino phenol can be achieved using more equivalents of the alkylsultone. Both of the resultant phenolic derivatives can be condensed with phthalic anhydride to make fluorophores as described.

According to an aspect of the invention there are provided dye compounds suitable for attachment to substrate moieties, particularly comprising linker groups to enable attachment to substrate moieties. Substrate moieties can be virtually any molecule or substance to which the dyes of the invention can be conjugated and, by way of non-limiting example, may include nucleosides, nucleotides, polynucleotides, carbohydrates, ligands, particles, solid surfaces, organic and inorganic polymers and combinations or assemblages thereof, such as chromosomes, nuclei, living cells and the like. The dyes can be conjugated by an optional linker by a variety of means including hydrophobic attraction, ionic attraction and covalent attachment. Particularly the dyes are conjugated to the substrate by covalent attachment. More particularly the covalent attachment is by means of a linker group.

The dyes according to the invention may include a reactive linker group at one of the substituent positions for covalent attachment of the dye to another molecule. Reactive linking groups are moieties capable of forming a covalent bond. In a particular embodiment the linker may be a cleavable linker. Use of the term "cleavable linker" is not meant to imply that the whole linker is required to be removed. The cleavage site can be located at a position on the linker that ensures that part of the linker remains attached to the dye and/or substrate moiety after cleavage. Cleavable linkers may be, by way of non-limiting example, electrophilically cleavable linkers, nucleophilically cleavable linkers, photocleavable linkers, cleavable under reductive conditions (for example disulfide or azide containing linkers), oxidative conditions, cleavable via use of safety-catch linkers and cleavable by elimination mechanisms. The use of a cleavable linker to attach the dye compound to a substrate moiety ensures that the label can, if required, be removed after detection, avoiding any interfering signal in downstream steps.

Particular linker groups may be found in pending patent application number WO2004/018493 (herein incorporated by reference) wherein the present inventors have found that certain linkers which connect the bases of nucleotides to labels such as, for example, dyes according to the present invention, may be cleaved using water-soluble phosphines or water-soluble transition metal catalysts formed from a transition metal and at least partially water-soluble ligands. In aqueous solution the latter form at least partially water-soluble transition metal complexes.

Particular linkers may be found in Applicants pending International application WO2004/018493 (herein incorporated by reference) and may comprise moieties of the formula:

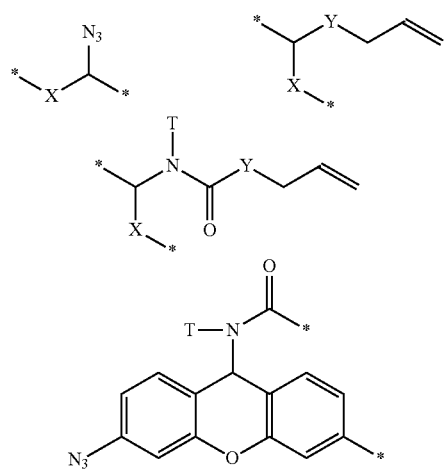

(wherein X is selected from the group comprising O, S, NH and NQ wherein Q is a C1-10 substituted or unsubstituted alkyl group, Y is selected from the group comprising O, S, NH and N(allyl), T is hydrogen or a C1-10 substituted or unsubstituted alkyl group and * indicates where the moiety is connected to the remainder of the nucleotide or nucleoside).

Still yet more particularly the inventors have determined in pending GB patent application number 0517097.2, published as WO07020457, (herein incorporated by reference) that by altering, and in particular increasing, the length of the linker between a fluorescent dye (fluorophore) and the guanine base, by introducing a polyethylene glycol spacer group, it is possible to increase the fluorescence intensity compared to the same fluorophore attached to the guanine base through other linkages known in the art. The design of the linkers, and especially their increased length, also allows improvements in the brightness of fluorophores attached to the guanine bases of guanosine nucleotides when incorporated into polynucleotides such as DNA. Thus, when the dye is for use in any method of analysis which requires detection of a fluorescent dye label attached to a guanine-containing nucleotide, it is advantageous if the linker comprises a spacer group of formula $((CH_2)_2O)_n$— wherein n is an integer between 2 and 50, as described in applicants pending application number GB0517097.2 (WO07020457).

The present invention further provides conjugates of nucleosides and nucleotides labelled with dyes according to the invention (modified nucleotides). Labelled nucleosides and nucleotides are useful for labelling polynucleotides formed by enzymatic synthesis, such as, by way of non-limiting example, in PCR amplification, isothermal amplification or solid phase amplification, polynucleotide sequencing including solid phase sequencing, nick translation reactions and the like.

Nucleosides and nucleotides may be labelled at sites on the sugar or nucleobase. As known in the art, a "nucleotide" consists of a nitrogenous base, a sugar, and one or more phosphate groups. In RNA the sugar is ribose and in DNA is a deoxyribose, i.e. a sugar lacking a hydroxyl group that is present in ribose. The nitrogenous base is a derivative of purine or pyrimidine. The purines are adenine (A) and guanine (G), and the pyrimidines are cytosine (C) and thymine (T) or in the context of RNA, uracil (U). The C-1 atom of deoxyribose is bonded to N-1 of a pyrimidine or N-9 of a purine. A nucleotide is also a phosphate ester of a nucleoside, with esterification occurring on the hydroxyl group attached to the C-3 or C-5 of the sugar. Nucleotides are usually mono, di- or triphosphates.

A "nucleoside" is structurally similar to a nucleotide but is missing the phosphate moieties. An example of a nucleoside analog would be one in which the label is linked to the base and there is no phosphate group attached to the sugar molecule.

Although the base is usually referred to as a purine or pyrimidine, the skilled person will appreciate that derivatives and analogues are available which do not alter the capability of the nucleotide or nucleoside to undergo Watson-Crick base pairing. "Derivative" or "analogue" means a compound or molecule whose core structure is the same as, or closely resembles that of a parent compound but which has a chemical or physical modification, such as, for example, a different or additional side group, which allows the derivative nucleotide or nucleoside to be linked to another molecule. For example, the base may be a deazapurine. The derivatives should be capable of undergoing Watson-Crick pairing. "Derivative" and "analogue" also mean a synthetic nucleotide or nucleoside derivative having modified base moieties and/or modified sugar moieties. Such derivatives and analogues are discussed in, for example, Scheit, Nucleotide analogs (John Wiley & Son, 1980) and Uhlman et al., Chemical Reviews 90:543-584, 1990. Nucleotide analogues can also comprise modified phosphodiester linkages including phosphorothioate, phosphorodithioate, alkyl-phosphonate, phosphoranilidate, phosphoramidate linkages and the like.

The dye may be attached to any position on the nucleotide base, through a linker, provided that Watson-Crick base pairing can still be carried out. Particular nucleobase labelling sites include the C5 position of a pyrimidine base or the C7 position of a 7-deaza purine base. As described above a linker group may be used to covalently attach a dye to the nucleoside or nucleotide.

In particular embodiments the labelled nucleoside or nucleotide may be enzymatically incorporable and enzymatically extendable. Accordingly a linker moiety may be of sufficient length to connect the nucleotide to the compound such that the compound does not significantly interfere with the overall binding and recognition of the nucleotide by a nucleic acid replication enzyme. Thus, the linker can also comprise a spacer unit. The spacer distances, for example, the nucleotide base from a cleavage site or label.

Nucleosides or nucleotides labelled with dyes of the invention may have the formula:

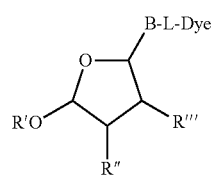

Where Dye is a dye compound according to the present invention, B is a nucleobase, such as, for example uracil, thymine, cytosine, adenine, guanine and the like and L is an optional linker group which may or may not be present. R' can be H, monophosphate, diphosphate, triphosphate, thiophosphate, a phosphate ester analog, —O— attached to a reactive phosphorous containing group or —O— protected by a blocking group. R" can be H, OH, a phosphoramidite or a 3'OH blocking group and R'" is H or OH.

Where R" is phosphoramidite, R' is an acid-cleavable hydroxyl protecting group which allows subsequent monomer coupling under automated synthesis conditions.

In a particular embodiment the blocking group is separate and independent of the dye compound, i.e. not attached to it. In an alternative embodiment the dye may comprise all or part of the 3'OH blocking group. Thus R" can be a 3'OH blocking group which may or may not comprise the dye compound.

In still yet another alternative embodiment there is no blocking group on the 3' carbon of the pentose sugar and the dye (or dye and linker construct) attached to the base, for example, can be of a size or structure sufficient to act as a block to the incorporation of a further nucleotide from a point other than the 3' site. Thus the block can be due to steric hindrance or can be due to a combination of size, charge and structure.

The use of a blocking group allows polymerisation to be controlled, such as by stopping extension when a modified nucleotide is incorporated. If the blocking effect is reversible, for example by way of non-limiting example by changing chemical conditions or by removal of a chemical block, extension can be stopped at certain points and then allowed to continue.

In another particular embodiment a 3'OH blocking group will comprise moieties disclosed in WO2004/018497 (herein incorporated by reference). For example the blocking group may be azidomethyl ($CH_2N_3$) or allyl.

In a particular embodiment the linker and blocking group are both present and are separate moieties which are both cleavable under substantially similar conditions. Thus deprotection and deblocking processes may be more efficient since only a single treatment will be required to remove both the dye compound and the block.

The invention also encompasses polynucleotides incorporating dye compounds according to the present invention. Such polynucleotides may be DNA or RNA comprised respectively of deoxyribonucleotides or ribonucleotides joined in phosphodiester linkage. Polynucleotides according to the invention may comprise naturally occurring nucleotides, non-naturally occurring (or modified) nucleotides other than the modified nucleotides of the invention or any combination thereof, provided that at least one modified nucleotide, i.e. labelled with a dye compound, according to the invention is present. Polynucleotides according to the invention may also include non-natural backbone linkages and/or non-nucleotide chemical modifications. Chimeric structures comprised of mixtures of ribonucleotides and deoxyribonucleotides comprising at least one modified nucleotide according to the invention are also contemplated.

Modified nucleotides (or nucleosides) comprising a dye compound according to the invention may be used in any method of analysis which requires detection of a fluorescent label attached to a nucleotide or nucleoside, whether on its own or incorporated into or associated with a larger molecular structure or conjugate. In this context the term "incorporated into a polynucleotide" requires that the 5' phosphate is joined in phosphodiester linkage to the 3' hydroxyl group of a second (modified or unmodified) nucleotide, which may itself form part of a longer polynucleotide chain. The 3' end of the modified nucleotide of the invention may or may not be joined in phosphodiester linkage to the 5' phosphate of a further (modified or unmodified) nucleotide. Thus, in one non-limiting embodiment the invention provides a method of detecting a modified nucleotide incorporated into a polynucleotide which comprises: (a) incorporating at least one modified nucleotide according to the third aspect of the invention into a polynucleotide and (b) detecting the modified nucleotide(s)

incorporated into the polynucleotide by detecting the fluorescent signal from the dye compound attached to said modified nucleotide(s).

This method requires two essential steps: a synthetic step (a) in which one or more modified nucleotides according to the invention are incorporated into a polynucleotide and a detection step (b) in which one or more modified nucleotide(s) incorporated into the polynucleotide are detected by detecting or quantitatively measuring their fluorescence.

In one embodiment of the invention the at least one modified nucleotide is incorporated into a polynucleotide in the synthetic step by the action of a polymerase enzyme. However, other methods of joining modified nucleotides to polynucleotides, such as for example chemical oligonucleotide synthesis or ligation of labelled oligonucleotides to unlabelled oligonucleotides, are not excluded. Therefore, in the specific context of this method of the invention, the term "incorporating" a nucleotide into a polynucleotide encompasses polynucleotide synthesis by chemical methods as well as enzymatic methods.

In a specific embodiment the synthetic step may comprise incubating a template polynucleotide strand with a reaction mixture comprising fluorescently labelled modified nucleotides of the invention and a polymerase under conditions which permit formation of a phosphodiester linkage between a free 3' hydroxyl group on a polynucleotide strand annealed to said template polynucleotide strand and a 5' phosphate group on said modified nucleotide. This embodiment comprises a synthetic step in which formation of a polynucleotide strand is directed by complementary base-pairing of nucleotides to a template strand.

In all embodiments of the method, the detection step may be carried out whilst the polynucleotide strand into which the modified nucleotides are incorporated is annealed to a template strand, or after a denaturation step in which the two strands are separated. Further steps, for example chemical or enzymatic reaction steps or purification steps, may be included between the synthetic step and the detection step. In particular, the target strand incorporating the modified nucleotide(s) may be isolated or purified and then processed further or used in a subsequent analysis. By way of example, target polynucleotides labelled with modified nucleotide(s) according to the invention in a synthetic step may be subsequently used as labelled probes or primers. In other embodiments the product of the synthetic step (a) may be subject to further reaction steps and, if desired, the product of these subsequent steps purified or isolated.

Suitable conditions for the synthetic step will be well known to those familiar with standard molecular biology techniques. In one embodiment the synthetic step may be analogous to a standard primer extension reaction using nucleotide precursors, including modified nucleotides according to the invention, to form an extended target strand complementary to the template strand in the presence of a suitable polymerase enzyme. In other embodiments the synthetic step may itself form part of an amplification reaction producing a labelled double stranded amplification product comprised of annealed complementary strands derived from copying of the target and template polynucleotide strands. Other exemplary "synthetic" steps include nick translation, strand displacement polymerisation, random primed DNA labelling etc. The polymerase enzyme used in the synthetic step must be capable of catalysing the incorporation of modified nucleotides according to the invention. Otherwise, the precise nature of the polymerase is not particularly limited but may depend upon the conditions of the synthetic reaction. By way of example, if the synthetic reaction is carried out using thermocycling then a thermostable polymerase is required, whereas this may not be essential for standard primer extension reactions. Suitable thermostable polymerases which are capable of incorporating the modified nucleotides according to the invention include those described in WO 2005/024010 or WO06120433. In synthetic reactions which are carried out at lower temperatures such as 37.degree. C., polymerase enzymes need not necessarily be thermostable polymerases, therefore the choice of polymerase will depend on a number of factors such as reaction temperature, pH, strand-displacing activity and the like.

In specific non-limiting embodiments the invention encompasses use of the modified nucleotides or nucleosides labelled with dyes according to the invention in a method of nucleic acid sequencing, re-sequencing, whole genome sequencing, single nucleotide polymorphism scoring, any other application involving the detection of the modified nucleotide or nucleoside when incorporated into a polynucleotide, or any other application requiring the use of polynucleotides labelled with the modified nucleotides comprising fluorescent dyes according to the invention.

In a particular embodiment the invention provides use of modified nucleotides comprising dye compounds according to the invention in a polynucleotide "sequencing-by-synthesis" reaction. Sequencing-by-synthesis generally involves sequential addition of one or more nucleotides or oligonucleotides to a growing polynucleotide chain in the 5' to 3' direction using a polymerase or ligase in order to form an extended polynucleotide chain complementary to the template nucleic acid to be sequenced. The identity of the base present in one or more of the added nucleotide(s) is determined in a detection or "imaging" step. The identity of the added base may be determined after each nucleotide incorporation step. The sequence of the template may then be inferred using conventional Watson-Crick base-pairing rules. The use of the modified nucleotides labelled with dyes according to the invention for determination of the identity of a single base may be useful, for example, in the scoring of single nucleotide polymorphisms, and such single base extension reactions are within the scope of this invention.

In an embodiment of the invention, the sequence of a template polynucleotide is determined by detecting the incorporation of one or more nucleotides into a nascent strand complementary to the template polynucleotide to be sequenced through the detection of fluorescent label(s) attached to the incorporated nucleotide(s). Sequencing of the template polynucleotide is primed with a suitable primer (or prepared as a hairpin construct which will contain the primer as part of the hairpin), and the nascent chain is extended in a stepwise manner by addition of nucleotides to the 3' end of the primer in a polymerase-catalysed reaction.

In particular embodiments each of the different nucleotide triphosphates (A, T, G and C) may be labelled with a unique fluorophore and also comprises a blocking group at the 3' position to prevent uncontrolled polymerisation. Alternatively one of the four nucleotides may be unlabelled (dark). The polymerase enzyme incorporates a nucleotide into the nascent chain complementary to the template polynucleotide, and the blocking group prevents further incorporation of nucleotides. Any unincorporated nucleotides are removed and the fluorescent signal from each incorporated nucleotide is "read" optically by suitable means, such as a charge-coupled device using laser excitation and suitable emission filters. The 3'-blocking group and fluorescent dye compounds are then removed (deprotected), particularly by the same chemical or enzymatic method, to expose the nascent chain for further nucleotide incorporation. Typically the identity of the incorporated nucleotide will be determined after each incorporation step but this is not strictly essential. Similarly, U.S. Pat. No. 5,302,509 discloses a method to sequence polynucleotides immobilised on a solid support. The method relies on the incorporation of fluorescently labelled, 3'-blocked nucleotides A, G, C and T into a growing strand complementary to the immobilised polynucleotide, in the presence of DNA polymerase. The polymerase incorporates a base complementary to the target polynucleotide, but is prevented from further addition by the 3'-blocking group. The label of the incorporated nucleotide can then be determined and the blocking group removed by chemical cleavage to allow further polymerisation to occur. The nucleic acid template to be sequenced in a sequencing-by-synthesis reaction may be any polynucleotide that it is desired to sequence. The nucleic acid template for a sequencing reaction will typically comprise a double stranded region having a free 3' hydroxyl group which serves as a primer or initiation point for the addition of further nucleotides in the sequencing reaction. The region of the template to be sequenced will overhang this free 3' hydroxyl group on the complementary strand. The overhanging region of the template to be sequenced may be single stranded but can be double-stranded, provided that a "nick is present" on the strand complementary to the template strand to be sequenced to provide a free 3' OH group for initiation of the sequencing reaction. In such embodiments sequencing may proceed by strand displacement. In certain embodiments a primer bearing the free 3' hydroxyl group may be added as a separate component (e.g. a short oligonucleotide) which hybridises to a single-stranded region of the template to be sequenced. Alternatively, the primer and the template strand to be sequenced may each form part of a partially self-complementary nucleic acid strand capable of forming an intra-molecular duplex, such as for example a hairpin loop structure. Hairpin polynucleotides and methods by which they may be attached to solid supports are disclosed in applicant's co-pending International application publication nos. WO0157248 and WO 2005/047301. Nucleotides are added successively to the free 3' hydroxyl group, resulting in synthesis of a polynucleotide chain in the 5' to 3' direction. The nature of the base which has been added may be determined, particularly but not necessarily after each nucleotide addition, thus providing sequence information for the nucleic acid template. The term "incorporation" of a nucleotide into a nucleic acid strand (or polynucleotide) in this context refers to joining of the nucleotide to the free 3' hydroxyl group of the nucleic acid strand via formation of a phosphodiester linkage with the 5' phosphate group of the nucleotide.

The nucleic acid template to be sequenced may be DNA or RNA, or even a hybrid molecule comprised of deoxynucleotides and ribonucleotides. The nucleic acid template may comprise naturally occurring and/or non-naturally occurring nucleotides and natural or non-natural backbone linkages, provided that these do not prevent copying of the template in the sequencing reaction.

In certain embodiments the nucleic acid template to be sequenced may be attached to a solid support via any suitable linkage method known in the art, for example via covalent attachment. In certain embodiments template polynucleotides may be attached directly to a solid support (e.g. a silica-based support). However, in other embodiments of the invention the surface of the solid support may be modified in some way so as to allow either direct covalent attachment of template polynucleotides, or to immobilise the template polynucleotides through a hydrogel or polyelectrolyte multilayer, which may itself be non-covalently attached to the solid support.

Arrays in which polynucleotides have been directly attached to silica-based supports are those for example disclosed in WO00006770, wherein polynucleotides are immobilised on a glass support by reaction between a pendant epoxide group on the glass with an internal amino group on the polynucleotide. In addition, Applicants disclose in a co-pending International patent application publication number WO2005/047301 arrays of polynucleotides attached to a solid support, e.g. for use in the preparation of SMAs, by reaction of a sulphur-based nucleophile with the solid support. A still further example of solid-supported template polynucleotides is where the template polynucleotides are attached to hydrogel supported upon silica-based or other solid supports. Silica-based supports are typically used to support hydrogels and hydrogel arrays as described in WO00/31148, WO01/01143, WO02/12566, WO03/014392, U.S. Pat. No. 6,465,178 and WO00/53812.

A particular surface to which template polynucleotides may be immobilised is a polyacrylamide hydrogel. Polyacrylamide hydrogels are described in the prior art, some of which is discussed above. However, a particular hydrogel is described in WO2005/065814.

DNA template molecules can be attached to beads or microparticles for the purposes of sequencing; for example as described in U.S. Pat. No. 6,172,218. Further examples of the preparation of bead libraries where each bead contains different DNA sequences can be found in the prior art (Nature. 437, 376-380 (2005); Science. 309, 5741, 1728-1732 (2005)). Sequencing of arrays of such beads using nucleotides as described is within the scope of the invention.

The template(s) to be sequenced may form part of an "array" on a solid support, in which case the array may take any convenient form. Thus, the method of the invention is applicable to all types of "high density" arrays, including single-molecule arrays, clustered arrays and bead arrays. Modified nucleotides labelled with dye compounds of the invention may be used for sequencing templates on essentially any type of array formed by immobilisation of nucleic acid molecules on a solid support, and more particularly any type of high-density array. However, the modified nucleotides labelled with dye compounds of the invention are particularly advantageous in the context of sequencing of clustered arrays.

In multi-polynucleotide or clustered arrays, distinct regions on the array comprise multiple polynucleotide template molecules. The term "clustered array" refers to an array wherein distinct regions or sites on the array comprise multiple polynucleotide molecules that are not individually resolvable by optical means. Depending on how the array is formed each site on the array may comprise multiple copies of one individual polynucleotide molecule or even multiple copies of a small number of different polynucleotide molecules (e.g. multiple copies of two complementary nucleic acid strands). Multi-polynucleotide or clustered arrays of nucleic acid molecules may be produced using techniques generally known in the art. By way of example, WO 98/44151 and WO00/18957 both describe methods of amplification of nucleic acids wherein both the template and amplification products remain immobilised on a solid support in order to form arrays comprised of clusters or "colonies" of immobilised nucleic acid molecules. The nucleic acid molecules present on the clustered arrays prepared according to these methods are suitable templates for sequencing using the modified nucleotides labelled with dye compounds of the invention.

The modified nucleotides labelled with dye compounds of the invention are also useful in sequencing of templates on single molecule arrays. The term "single molecule array" or "SMA" as used herein refers to a population of polynucleotide molecules, distributed (or arrayed) over a solid support, wherein the spacing of any individual polynucleotide from all others of the population is such that it is possible to effect individual resolution of the polynucleotides. The target nucleic acid molecules immobilised onto the surface of the solid support should thus be capable of being resolved by optical means. This means that, within the resolvable area of the particular imaging device used, there must be one or more distinct signals, each representing one polynucleotide.

This may be achieved wherein the spacing between adjacent polynucleotide molecules on the array is at least 100 nm, more particularly at least 250 nm, still more particularly at least 300 nm, even more particularly at least 350 nm. Thus, each molecule is individually resolvable and detectable as a single molecule fluorescent point, and fluorescence from said single molecule fluorescent point also exhibits single step photobleaching.

The terms "individually resolved" and "individual resolution" are used herein to specify that, when visualised, it is possible to distinguish one molecule on the array from its neighbouring molecules. Separation between individual molecules on the array will be determined, in part, by the particular technique used to resolve the individual molecules. The general features of single molecule arrays will be understood by reference to published applications WO00/06770 and WO 01/57248. Although one use of the modified nucleotides of the invention is in sequencing-by-synthesis reactions, the utility of the modified nucleotides is not limited to such methods. In fact, the nucleotides may be used advantageously in any sequencing methodology which requires detection of fluorescent labels attached to nucleotides incorporated into a polynucleotide.

In particular, the modified nucleotides labelled with dye compounds of the invention may be used in automated fluorescent sequencing protocols, particularly fluorescent dye-terminator cycle sequencing based on the chain termination sequencing method of Sanger and co-workers. Such methods generally use enzymes and cycle sequencing to incorporate fluorescently labelled dideoxynucleotides in a primer extension sequencing reaction. So called Sanger sequencing methods, and related protocols (Sanger-type), rely upon randomised chain termination with labelled dideoxynucleotides.

Thus, the invention also encompasses modified nucleotides labelled with dye compounds according to the invention which are dideoxynucleotides lacking hydroxyl groups at both of the 3' and 2' positions, such modified dideoxynucleotides being suitable for use in Sanger type sequencing methods and the like.

Modified nucleotides labelled with dye compounds of the present invention incorporating 3' blocking groups, it will be recognized, may also be of utility in Sanger methods and related protocols since the same effect achieved by using modified dideoxy nucleotides may be achieved by using modified nucleotides having 3'-OH blocking groups: both prevent incorporation of subsequent nucleotides. Where nucleotides according to the present invention, and having a 3' blocking group are to be used in Sanger-type sequencing methods it will be appreciated that the dye compounds or detectable labels attached to the nucleotides need not be connected via cleavable linkers, since in each instance where a labelled nucleotide of the invention is incorporated; no nucleotides need to be subsequently incorporated and thus the label need not be removed from the nucleotide.

The invention also provides kits including modified nucleosides and/or nucleotides labelled with dyes according to the invention. Such kits will generally include at least one modified nucleotide or nucleoside labelled with a dye according to the invention together with at least one further component. The further component(s) may be further modified or unmodified nucleotides or nucleosides. For example, modified nucleotides labelled with dyes according to the invention may be supplied in combination with unlabelled or native nucleotides, and/or with fluorescently labelled nucleotides or any combination thereof. Accordingly the kits may comprise modified nucleotides labelled with dyes according to the invention and modified nucleotides labelled with other, for example, prior art dye compounds. Combinations of nucleotides may be provided as separate individual components or as nucleotide mixtures.

Where kits comprise a plurality, particularly two, more particularly four, modified nucleotides labelled with a dye compound, the different nucleotides may be labelled with different dye compounds, or one may be dark, with no dye compounds. Where the different nucleotides are labelled with different dye compounds it is a feature of the kits that said dye compounds are spectrally distinguishable fluorescent dyes. As used herein, the term "spectrally distinguishable fluorescent dyes" refers to fluorescent dyes that emit fluorescent energy at wavelengths that can be distinguished by fluorescent detection equipment (for example, a commercial capillary based DNA sequencing platform) when two or more such dyes are present in one sample. When two modified nucleotides labelled with fluorescent dye compounds are supplied in kit form, it is a feature of the invention that the spectrally distinguishable fluorescent dyes can be excited at the same wavelength, such as, for example by the same laser. When four modified nucleotides labelled with fluorescent dye compounds are supplied in kit form, it is a feature of the invention that two of the spectrally distinguishable fluorescent dyes can both be excited at one wavelength and the other two spectrally distinguishable dyes can both be excited at another wavelength. Particular excitation wavelengths are 532 nm, 630 nm to 700 nm, particularly 660 nm.

In one embodiment a kit comprises a modified nucleotide labelled with a compound of the invention and a second modified nucleotide labelled with a second dye wherein the dyes have a difference in absorbance maximum of at least 10 nm, particularly 20 nm to 50 nm. More particularly the two dye compounds have Stokes shifts of between 15-40 nm where "Stokes shift" is the distance between the peak absorption and peak emission wavelengths.

In a further embodiment said kit further comprises two other modified nucleotides labelled with fluorescent dyes wherein said dyes are excited by the same laser at 600 nm to 700 nm, particularly 630 nm to 700 nm, more particularly 660 nm. Wherein the dyes have a difference in absorbance maximum of at least 10 nm, particularly 20 nm to 50 nm. More particularly the two dye compounds have Stokes shifts of between 20-40 nm. Still yet more particularly the two dye compounds have a different absorbance maximum above 600 nm, particularly above 640 nm. Particular dyes which are spectrally distinguishable from rhodamine dyes of the invention and which meet the above criteria are polymethine analogues as described in U.S. Pat. No. 5,268,486 (for example Cy5) or WO 0226891 (Alexa 647; Molecular Probes A20106) or unsymmetrical polymethines as disclosed in U.S. Pat. No. 6,924,372.

In an alternative embodiment, the kits of the invention may contain nucleotides where the same base is labelled with two different compounds. A first nucleotide may be labelled with a compound of the invention. A second nucleotide may be labelled with a spectrally distinct compound, for example a 'red' dye absorbing at greater than 600 nm. A third nucleotide may be labelled as a mixture of the compound of the invention and the spectrally distinct compound, and the fourth nucleotide may be 'dark' and contain no label. In simple terms therefore the nucleotides 1-4 may be labelled 'green', 'red', 'red/green', and dark. To simplify the instrumentation further, four nucleotides can be labelled with a two dyes excited with a single laser, and thus the labelling of nucleotides 1-4 may be 'green 1', 'green 2' 'green 1/green 2', and dark.

Nucleotides may contain two dyes of the present invention. Dyes where $R_1$ and $R_4$ are H absorb at a lower wavelength than where $R_1$ and $R_4$ are alkyl. A kit may contain two or more nucleotides labelled with dyes of the invention. A kit may contain a nucleotide labelled with a compound of the invention where $R_1$ and $R_4$ are H, and a second nucleotide labelled with a compound of the invention where $R_1$ and $R_4$ are alkyl. Kits may contain a further nucleotide where a portion of the nucleotide is labelled with a compound of the invention where $R_1$ and $R_4$ are H, and a second portion of the nucleotide labelled with a compound of the invention where $R_1$ and $R_4$ are alkyl. Kits may further contain an unlabelled nucleotide.

In other embodiments the kits may include a polymerase enzyme capable of catalyzing incorporation of the modified nucleotides into a polynucleotide. Other components to be included in such kits may include buffers and the like. The modified nucleotides labelled with dyes according to the invention, and other any nucleotide components including mixtures of different nucleotides, may be provided in the kit in a concentrated form to be diluted prior to use. In such embodiments a suitable dilution buffer may also be included.

It is noted that, as used in this specification and the appended claims, the singular forms "a", "an" and "the" include plural referents unless expressly and unequivocally limited to one referent. It will be apparent to those skilled in the art that various modifications and variations can be made to various embodiments described herein without departing from the spirit or scope of the present teachings. Thus, it is intended that the various embodiments described herein cover other modifications and variations within the scope of the appended claims and their equivalents.

Experimental Details

Diethyl 4-hydroxyphthalate (2.1)

This compound was prepared from 4-hydroxy-phthalic acid 2.0 by an esterification with an excess of ethanol (absolute) in the presence of concentrated sulphuric acid.

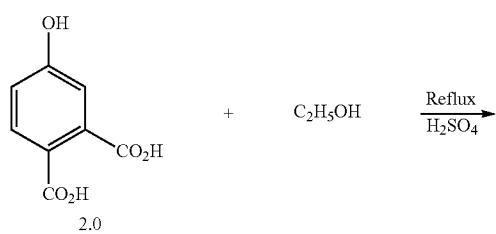

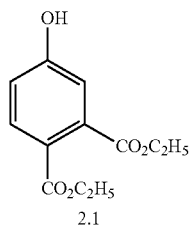

Preparation:

To a 0.5 L round bottomed flask containing absolute ethanol (250 ml, ~200 g, ~4.3 mol) 4-hydroxyphthalic acid 2.0 (15 g, 82.4 mmol) was added in a few portions at room temperature with stirring. This was then followed by an addition of 0.5 ml (~0.92 g, 9.4 mmol) of concentrated sulphuric acid. This mixture was stirred at room temperature for half an hour, and then it was further refluxed for 24 hours with a condenser.

About a half of solvent volume was distilled off using a descended condenser and the remaining solvent was removed under a reduced pressure. The viscous oily residue was dissolved in 400 ml DCM. To this solution, 1.5 g anhydrous potassium carbonate was added carefully in small portions. This mixture was kept at room temperature with stirring for about 2 hours, than filtered through ~100 g of silica gels. The silica gels were further washed with DCM to elute more absorbed products. The combined organic fractions were dried with anhydrous magnesium sulphate (~5 g) overnight. Solids were filtered off, and further washed with DCM. Solvent was evaporated under a reduced pressure.

This ester 2.1 obtained as colourless oily product was used in the next step without further purification.

Yield: 22 g (~99%)

$^1$H NMR: (400 MHz, DMSO-$d_6$) δ 10.59 (s, 1H), 7.68 (d, J=8.5 Hz, 1H), 7.07-6.76 (m, 2H), 4.22 (dq, J=13.4, 7.1 Hz, 4H), 1.25 (td, J=7.1, 3.3 Hz, 6H).

Diethyl 4-[(3-ethoxycarbonyl)propyloxy]phthalate (2.2)

This compound was prepared in ethanol from diethyl 4-hydroxyphthalate 2.1 via beforehand formation of potassium 3,4-bis(ethoxycarbonyl)phenolate and then by alkylation with ethyl 4-bromobutyrate in the same reaction pot.

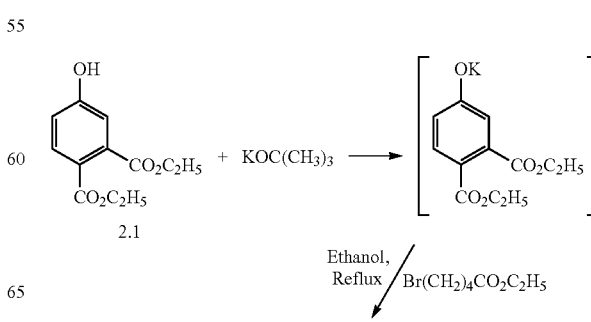

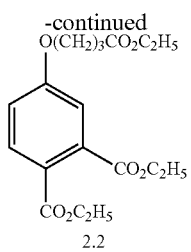

2.2

Preparation:

To a solution of the ester 2.1 (2 g, 8.4 mmol) in absolute ethanol (20 ml), solid potassium tert-butoxide (1.1 g, 9.8 mmol, 1.15 eq) was added slowly. The reaction mixture was kept at room temperature for an hour, and then ethyl 4-bromobutyrate (2 g, ~1.5 ml) was added. The reaction was kept at room temperature for an hour, and then was heated under reflux with a condenser overnight.

The reaction mixture was chilled (up to about 0-5° C.) with an ice-bath for 3-4 hours. Inorganic precipitates were filtered off and further washed with a cold absolute ethanol. The precipitates were discarded and the combined filtrates were concentrated under reduced pressure.

The residue that contained some inorganic solids was diluted with a mixture of DCM-Petroleum ether (7:3, 50 ml) and filtered through of a short plug of Silica Gels (~10 g). Silica Gels were further washed with DCM-MeOH (97:3, ~150 ml) to elute more absorbed product (TLC was used to monitor the completion of product elution; use more eluent solvent if needed). The combined organic fractions were dried with anhydrous magnesium sulphate (~1 g) overnight and evaporated under a reduced pressure. This ester 2.2 was used in the next step without further purification. Yield: 2 g (67.6%)

$^1$H NMR: (400 MHz, Methanol-$d_4$) δ 7.87-7.77 (m, 1H), 7.18-7.05 (m, 2H), 4.33 (dq, J=14.5, 7.1 Hz, 4H), 4.21-4.07 (m, 4H), 2.53 (t, J=7.3 Hz, 2H), 2.17-2.04 (m, 2H), 1.36 (td, J=7.1, 3.5 Hz, 6H), 1.25 (t, J=7.2 Hz, 3H).

4-(3-Carboxypropyloxy)phthalic acid (2.3)

This derivative of phthalic acid was prepared by a saponification of the triethyl ester 2.2 from previous step by an aqueous solution of sodium hydroxide.

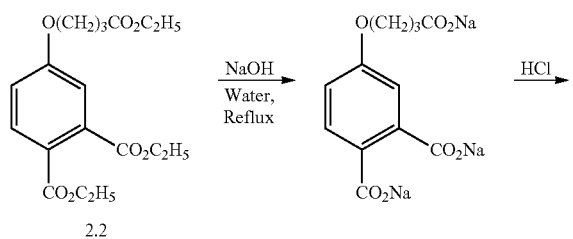

Preparation:

To a round bottomed flask, equipped with a stirrer and a condenser, 100 ml de-ionised water was poured and NaOH (5 g, 125 mmol) were then added in small portions. After sodium hydroxide was dissolved, the triethyl ester 2.2 (10.5 g, ~30 mmol) was added. The reaction mixture was vigorously stirred at 110° C. (heating block) for 5 hours. After about 3 hours, the oily starting material 2.2 was dissolved. The reaction solution was filtered and the filtrate collected was transfer to a round-bottomed flask. About 10-15 ml of liquid containing ethanol formed during the reaction and water, was distilled off with a descent condenser. The remaining solution was cooled by ice-bath (0-5° C.).

To this cold solution, concentrated hydrochloric acid (37%, 11 ml, 135 mmol) was added slowly with stirring. The pH of this mixture was checked by an indicator to ensure an excess of mineral acid. The expected product as a white precipitate was formed soon after this. The mixture was kept at ~0-5° C. for an hour. The precipitate was filtered, washed with a few ml of cold water and then dried overnight.

This product 2.3 was used in the next step without further purification. However, it could be purified by crystallization from water if necessary. Yield: 5.1 g, 64%

$^1$H-NMR:

(400 MHz, $CF_3COO$-d) δ 11.62 (d, J=1.5 Hz, 6H), 8.10 (dd, J=8.8, 1.5 Hz, 1H), 7.36 (d, J=2.4 Hz, 1H), 7.23-7.14 (m, 1H), 4.24 (td, J=5.9, 1.6 Hz, 2H), 2.76 (td, J=7.2, 1.6 Hz, 2H), 2.35-2.24 (m, 2H).

4-(3-Carboxypropyloxy)phthalic anhydride (2.4)

Preparation of the anhydride 2.4 can be accomplished by reaction of the acid 2.3 with dehydrating reagents like acetic anhydride, preheating of the acid 2.3 at high temperatures or just by keeping the acid 2.3 in a dissector with an inorganic dehydrating reagent.

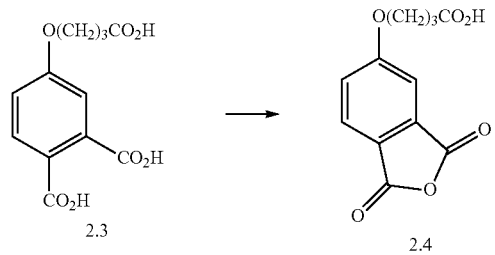

4-Acetyloxyphthalic anhydride (2.5)

This compound was prepared from 4-hydroxy-phthalic acid 2.0 by dehydratation with an excess acetic anhydride in according with procedure published in literature (Synthesis 2008, p. 3415).

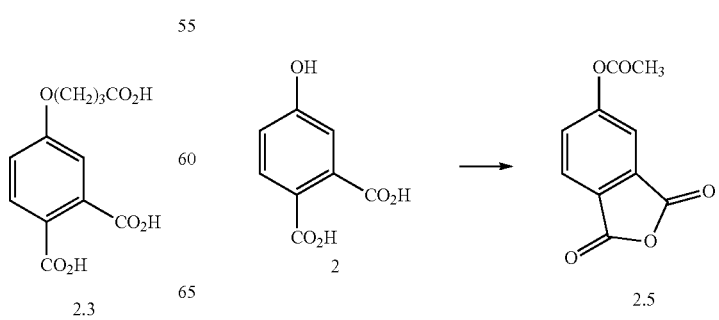

To a solution of 4-hydroxyphthalic acid 2 (5.39 g) in toluene (100 ml) acetic anhydride (25 ml) was added and mixture was refluxed for 2 h. Next day the crystallized product was filtered off. Yield 2.6 g (42.5%).

The Dye (XI-1) Synthesis:

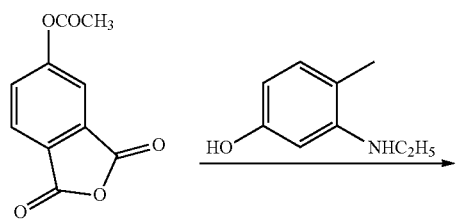

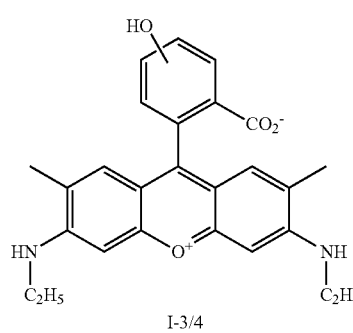

To a round-bottomed flask, 4-acetyloxyphtalic acid (1.03 g), 3-ethylamino-cresol (2.0 g) and potassium pyrosulphate (1.5 g) were added. The reagents were carefully mixed together with a spatula and heated at 150° C. (heating block) for 6 h. During this time more and more intensive red colour was developed and reaction mixture solidified. Both TLC (acetonitrile-water, 20%) and HPLC (@ 280 nm) were used to check the reaction progress by monitoring the ratio of dyes and the starting 3-ethylaminocresol. After about 5 hours this ratio remained roughly constant. To the reaction mixture 10 ml water was added and pink coloured product filtered off. The precipitate was placed into a round-bottomed flask, methanol (50 ml) added and mixture refluxed for 10 min. About a ¾ of the solvent was removed in vacuum and this red coloured solution was left overnight. Product as red crystals was filtered off. Yield 1 g (46%).

If needed isomers may be separated by chromatography.

The Dye (I) Synthesis:

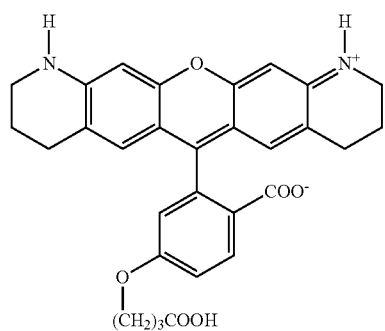

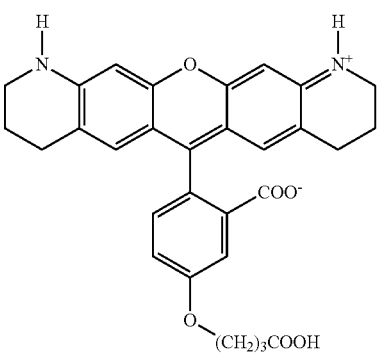

Target compounds as a mixture of constitutional isomers were synthesized by a condensation of the phthalic acid 2.3 with 7-hydroxy-1,2,3,4-tetrahydroquinoline at high temperature. Reaction fulfilled by using anhydrous phosphoric acid as a catalyst and solvent as well.

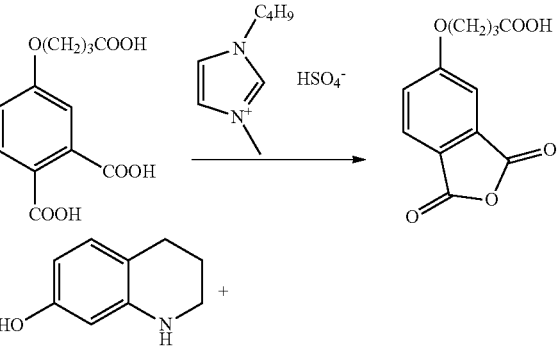

Dye (I-1) and (I-2) Reaction Scheme:

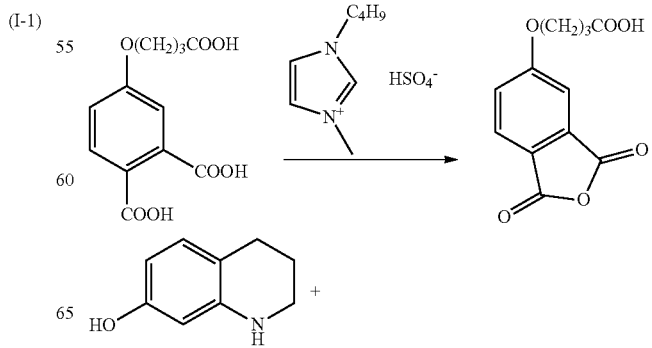

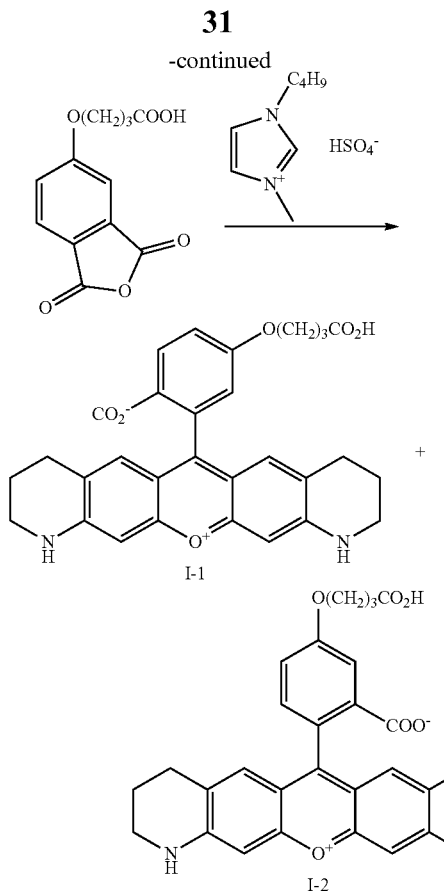

Preparation:

4-(3-carboxypropoxy)phthalic acid (0.268 g) and 0.5 g of 1-butyl-3-methyl-imidazolium hydrosulphate (IL-HSO$_4$) was heated 1 h at 125° C. for completion of anhydride (Xa-2.4) formation. 7-Hydroxy-tetrahydro-dihydroquinolin (0.298 g) was added and the reaction mixture was stirred at 175° C. for 2 h.

Red coloured compound with strong fluorescent formed. TLC control in CH$_3$CN-water (4:1) confirmed dyes formation. Heating at 175° C. was continued for additional 3 h.

This crude material was dissolved in CH$_3$CN-water mixture (10%) and purified by flash column chromatography on Silica-gel. Red coloured fractions were collected and solvents evaporated.

Dye (I-1): Yield 18 mg (16%).

Dye (I-2): Yield 9 mg (8%).

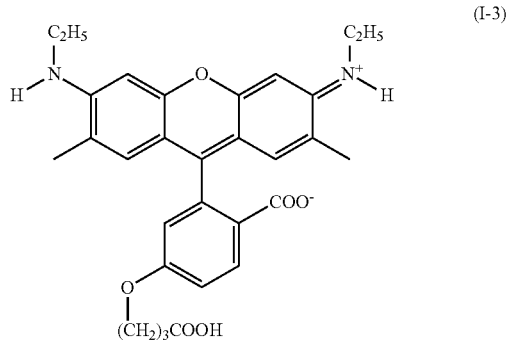

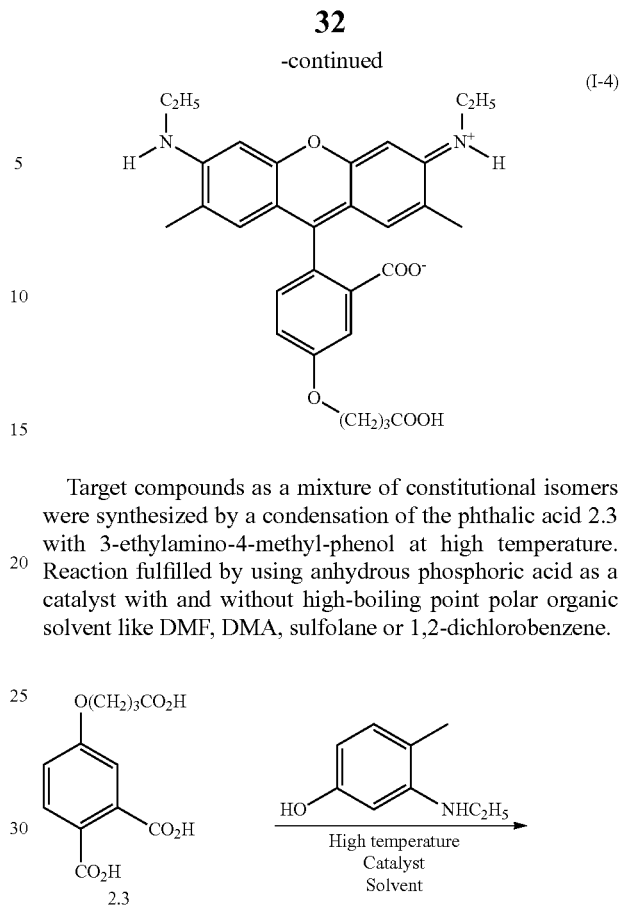

Target compounds as a mixture of constitutional isomers were synthesized by a condensation of the phthalic acid 2.3 with 3-ethylamino-4-methyl-phenol at high temperature. Reaction fulfilled by using anhydrous phosphoric acid as a catalyst with and without high-boiling point polar organic solvent like DMF, DMA, sulfolane or 1,2-dichlorobenzene.

This reaction can be carried out using potassium disulphate as a catalyst. This reagent acts as a mild Lewis acid, which may stimulate the formation and/or further reactions of the starting materials and/or intermediates formed. As a result, the reaction temperature was lower and the amount of side products was reduced. The nature of a catalyst and a solvent been used exert a significant effect not only on the reaction yield and purity of the products but also on the regio-selectivity of the isomeric dyes formation. In this way formation of one or another isomer as a prevalent one can be achieved.

Additionally some ionic liquids (IL) can improve the rhodamine dye formation both on reaction yield and product purity. We also have achieved definitive improvement with some IL on the synthesis of the dyes (I). Among the IL (1-ethyl-3-methyl-imidazolium quaternary salts family and some tetra-alkyl ammonium salts) we tested, some efficiently promote the formation of one or another isomer and furnish a cleaner product (fewer coloured by-products in the reaction mixture).

Dyes (I-3) and (I-4)
Chemical Name:
  (I-3): 3,6-Bis(ethylamino)-2,7-dimethyl-[2-carboxylato-5-(3-carboxypropyloxy)phenyl]xanthylium betaine
  (I-4): 3,6-Bis(ethylamino)-2,7-dimethyl-[2-carboxylato-4-(3-carboxypropyloxy)phenyl]xanthylium betaine Reaction Scheme:

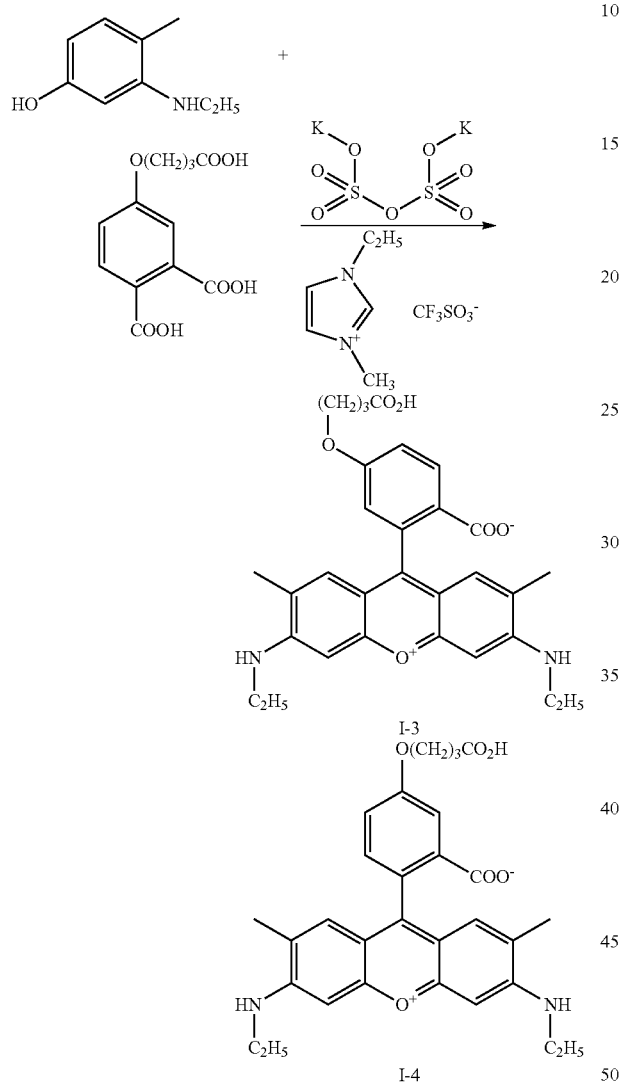

Preparation:
To a round-bottomed flask, 4-carboxypropyloxyphtalic acid (1.0 g, 3.73 mmol), 3-ethylamino-cresol (2.0 g, 13.23 mmol), IL-CF3 (1.72 g, 6.61 mmol) and potassium pyrosulphate (1.68 g, 6.61 mmol) were added. The reagents were carefully mixed together with a spatula and heated at 150° C. (heating block) for 10 h. During this time more and more intensive red colour was developed and reaction mixture solidified.

Both TLC (acetonitrile-water, 20%) and HPLC (@ 280 nm) were used to check the reaction progress by monitoring the ratio of dyes and the starting 3-ethylaminocresol. After 10 hours this ratio remained roughly constant.

Reaction mixture was cooled to room temperature, and the red solid was dissolved in methanol (~20 ml). The colourless insoluble inorganic materials were filtered off. Triethylamine (2 ml) was added to the filtrate and the resulting solution was applied to Biotage $C_{18}$ samplet (40 g). The samplet was then dried in vacuum to remove most of solvents.

Product was isolated by flash chromatography on Biotage Isolera-4 instrument on a 400 g $C_{18}$ column using mixture of 0.1M TEAB in water and acetonitrile as eluting solvents (gradient 17-27). Product collection wavelength was set at 520 nm, and the control wavelength was set at 280 nm to monitor separation from excess of the starting materials and colourless side products formed.

Yellow-orange coloured fractions were collected. Solvents were removed by a rotary evaporator in vacuum. The remaining solid red residue was triturated with petroleum ether (60-95° C., 25 ml) and product, 1-3 as a red powder was filtered off and dried on air.

Yield: 0.50 g (29%).
(I-3):
$^1$H-NMR:
(400 MHz, DMSO-$d_6$) δ 7.84 (d, J=8.5 Hz, 1H), 7.18 (dd, J=8.5, 2.2 Hz, 1H), 6.58 (d, J=2.2 Hz, 1H), 6.30 (s, 2H), 6.25 (s, 2H), 5.26 (t, J=5.4 Hz, 2H), 3.95 (t, J=6.4 Hz, 2H), 3.22-3.10 (m, 4H), 2.30 (d, J=7.3 Hz, 2H), 1.91 (s, 8H), 1.21 (t, J=7.1 Hz, 6H).
(I-4):
Yield: 0.16 g (9%).
Dye (I-5) I-3-NHS Reaction Scheme:

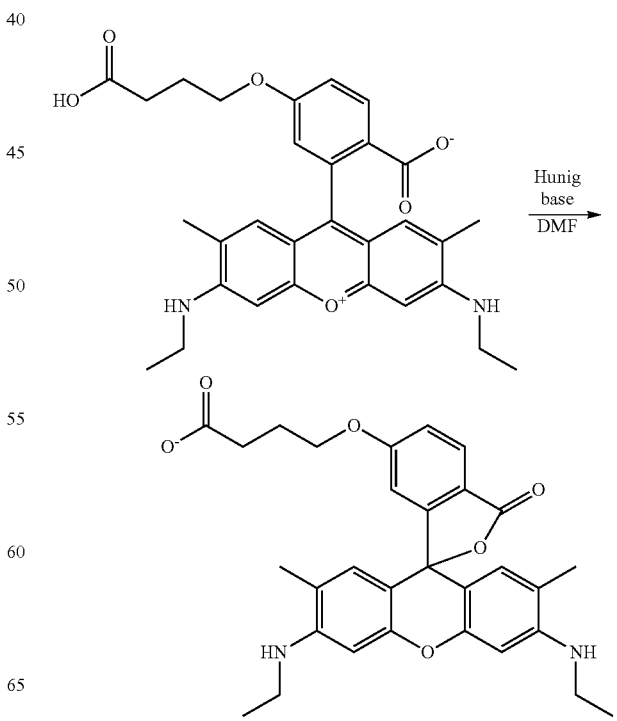

-continued

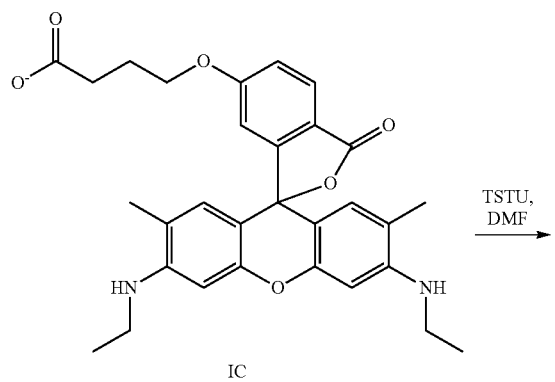
IC

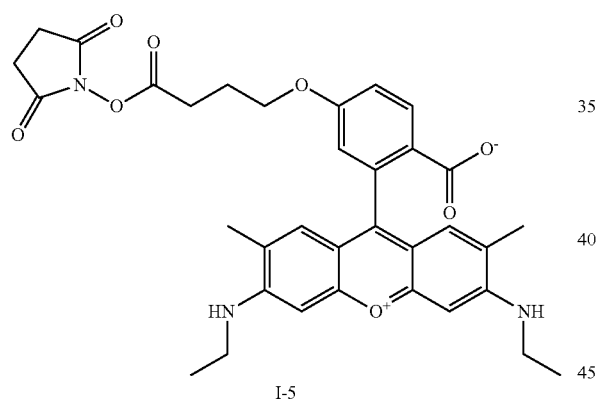
I-5

Preparation:

The dye (I-3) was dried under high vacuum overnight then 35 mg sample (68 μmol) taken and was placed into round-bottomed flask. Anhydrous DMF (3 mL) and Hunig's base (678 μmol, 116 μL) was added to the flask. Mixture (became nearly colourless due to formation of cyclic derivative (IC) and was stirred for about 20 min under nitrogen atmosphere. TSTU (80 μmol, 25 mg) was then added. A light pink colour developed. The reaction mixture was stirred at room temperature for 1 h, Progress was checked by TLC, (20% $H_2O$ in $CH_3CN$). This lactone could be isolated by precipitation from solution, or just distillation of the solvent in vacuum. The NHS ester (I-5) prepared in this way was used for coupling without further purification and isolation from solution. If needed the NHS ester could be isolated from solution by precipitation, for example, by precipitation with ethyl acetate, filtered off and dried.

Dye (I-6) I-3-PEG12

Reaction Scheme:

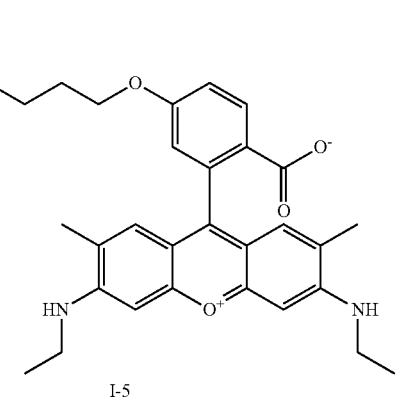
I-5

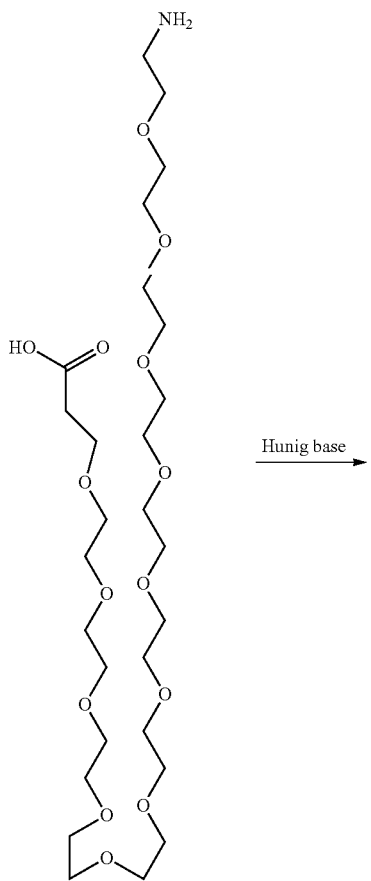

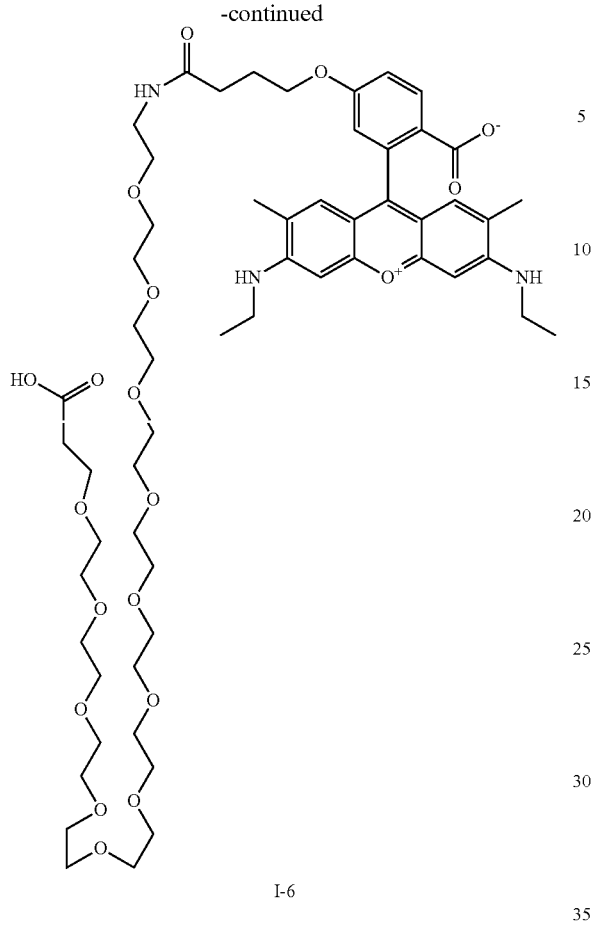

I-6

Preparation:

A solution of NH₂Peg12COOH (203 μmol, 126 mg) in water (300 μL) was added to the solution of (I-5) prepared as described above and the reaction mixture was stirred at room temperature overnight. Completion of the reaction been checked by TLC (20% H₂O in acetonitrile). After coupling completion, 0.1M TEAB solution in water (4 mL) was added and the mixture was stirred at ~20° C. for 1 h to quench reactive intermediates. The solvents were removed under vacuum. Residue was dissolved in 10 ml 0.1M TEAB. This solution filtered through a syringe filter 0.2 nm pore size and was transferred into two 5 mL HPLC vials for HPLC purification. The product was purified by HPLC using C18 reverse phase column with acetonitrile-0.1M TEAB. Fractions with absorption max 526 nm were collected. Yield 47 μmol (70%).

Dye (I-7) I-4-NHS

Reaction Scheme:

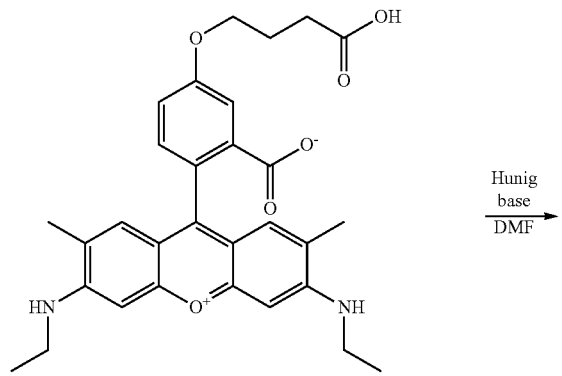

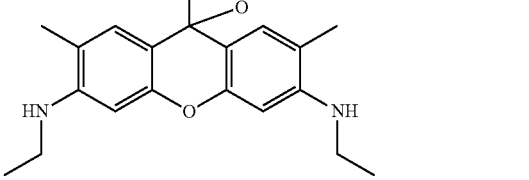

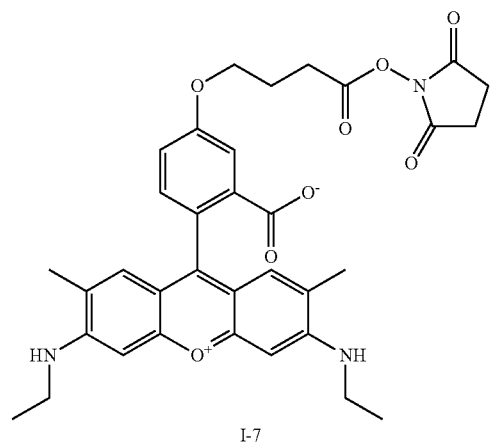

IC1

I-7

Preparation:

The dye (I-4) was dried under high vacuum overnight then 28 mg sample taken. Anhydrous DMF (3 mL) and Hunig base was added to the flask. Mixture became nearly colourless. Solution of cyclic form been stirred for about 20 min under nitrogen atmosphere. TSTU (25 mg) was then added. Light pink colour developed. Reaction mixture was stirred at RT for 1 h. Progress was checked by TLC, (20% H₂O in MeCN). NHS-ester R_f ~0.7. Activation was completed in 2 h.

The NHS ester (I-7) prepared in this way was used for coupling without further purification and isolation from solution. If needed the NHS ester could be isolated from solution by precipitation with ethyl acetate, filtered off and dried.

Dye (I-8) I-4-PEG12

Reaction Scheme:

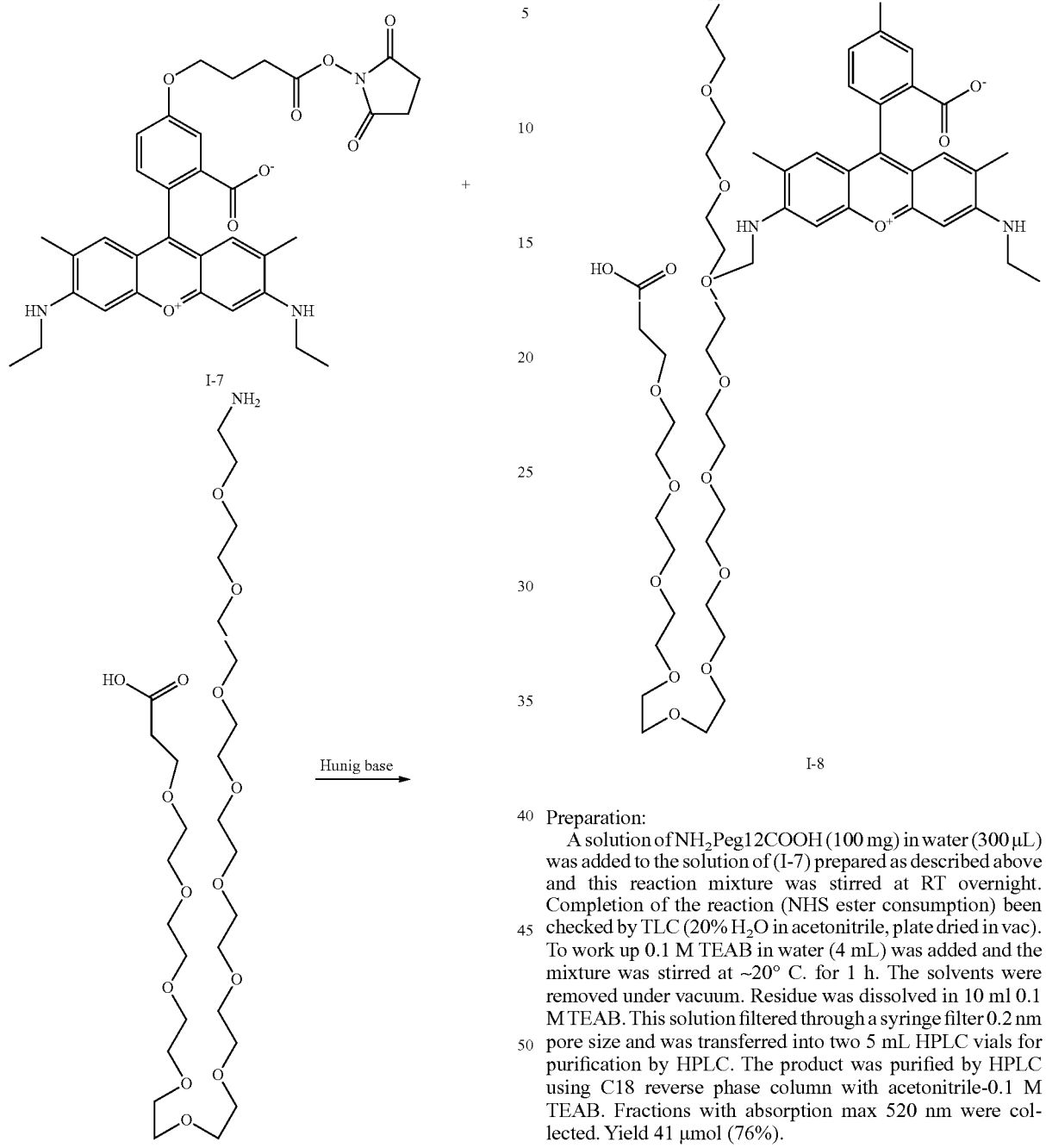

Preparation:

A solution of NH₂Peg12COOH (100 mg) in water (300 μL) was added to the solution of (I-7) prepared as described above and this reaction mixture was stirred at RT overnight. Completion of the reaction (NHS ester consumption) been checked by TLC (20% H₂O in acetonitrile, plate dried in vac). To work up 0.1 M TEAB in water (4 mL) was added and the mixture was stirred at ~20° C. for 1 h. The solvents were removed under vacuum. Residue was dissolved in 10 ml 0.1 M TEAB. This solution filtered through a syringe filter 0.2 nm pore size and was transferred into two 5 mL HPLC vials for purification by HPLC. The product was purified by HPLC using C18 reverse phase column with acetonitrile-0.1 M TEAB. Fractions with absorption max 520 nm were collected. Yield 41 μmol (76%).

Dye (I-9) pppG-I-3-PEG12

Reaction Scheme:
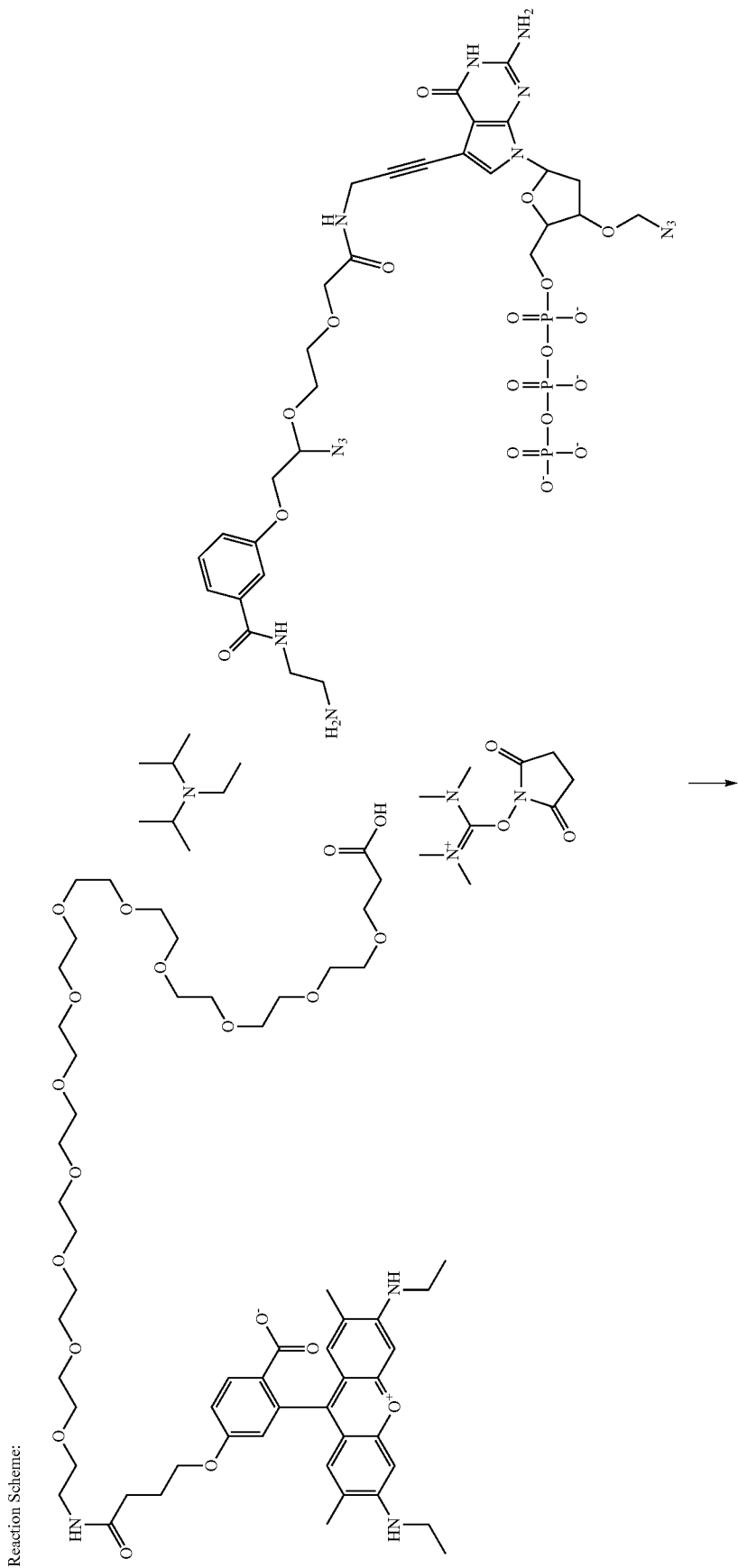

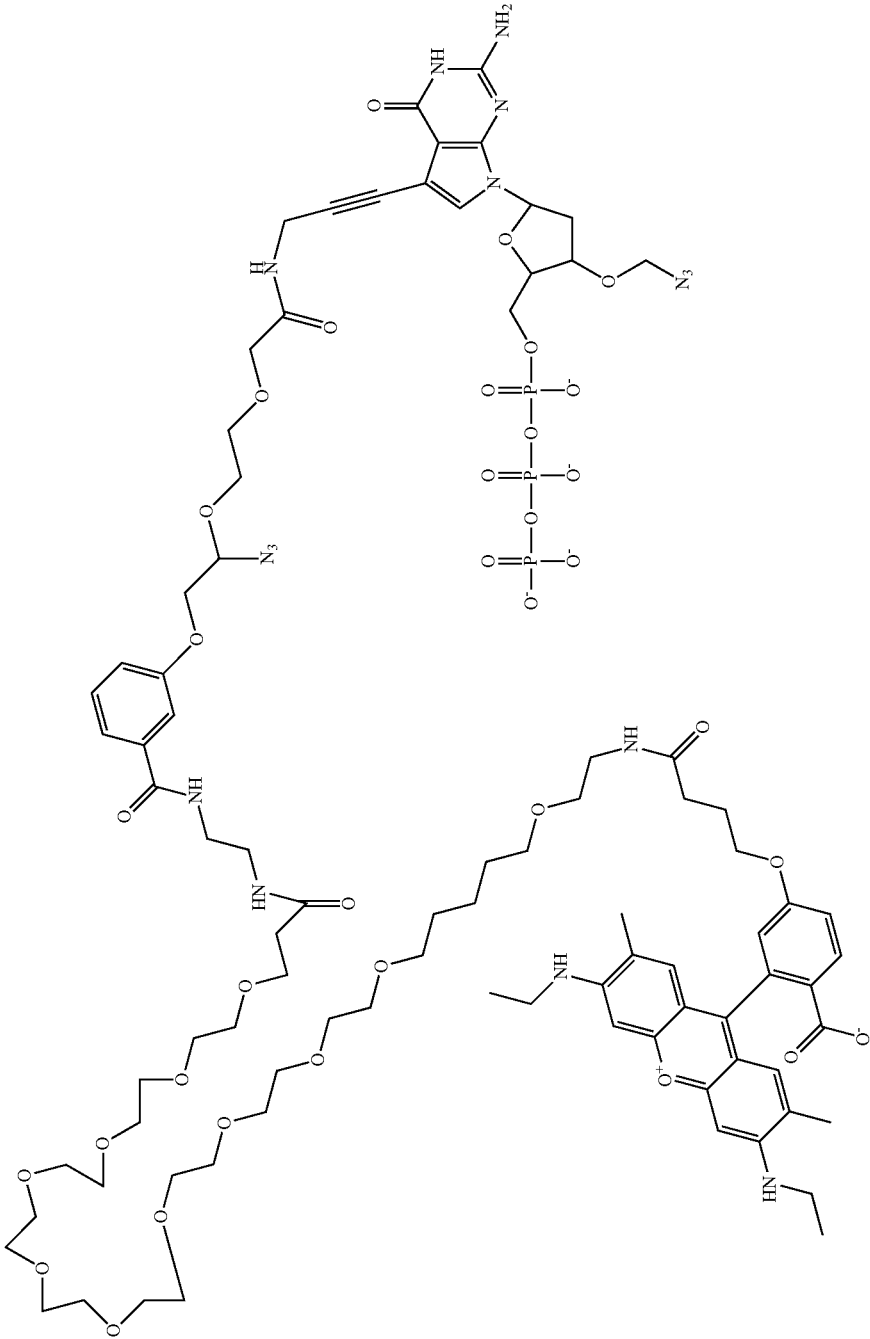

Preparation:

Anhydrous DMA (7 mL) and Hunig's Base (0.082 mL) were added to the dried sample (52 mg) of (I-6). A solution of TSTU (17 mg) in 1 mL of dry DMA was then added. System was flushed two times with nitrogen and then reaction mixture was stirred at room temperature for 1 h, According TLC (20% $H_2O$ in $CH_3CN$) activation completed.

Once the activation is started a solution of pppG-LN3 (3 mL of stock 3.5 mM) vac down to dryness. After activation was completed this solution was added to pppG. The reaction was stirred at room temperature under nitrogen atmosphere for 3 h. TLC control in 20% $H_2O$ in acetonitrile. Reaction mixture was cooled down to −4° C. with an ice-bath, 0.1 M TEAB (4 mL) was then added and the mixture was stirred at room temperature for 10 min.

Purification: The solution was applied to column with ~20 g of suspension of DEAE sephadex resin in 0.05 M TEAB solution and washed with TEAB from 0.1 M up to 0.4 M. Coloured fractions were combined, co-evaporated with water to remove more TEAB and vac down to dryness.

The residue was then re-dissolve in TEAB 0.1 M. This solution was filtered through a syringe filter 0.2 nm pore size into a corning flask, and then transferred into high recovery 5 mL HPLC vials for HPLC purification. The solution can be stored in the freezer until purification. The product was purified by HPLC using C18 reverse phase column with acetonitrile-0.1 M TEAB as eluents, Fractions with absorption 525 nm were collected. Yield: 54%.

Dye (I-10) pppG-I-4-PEG12

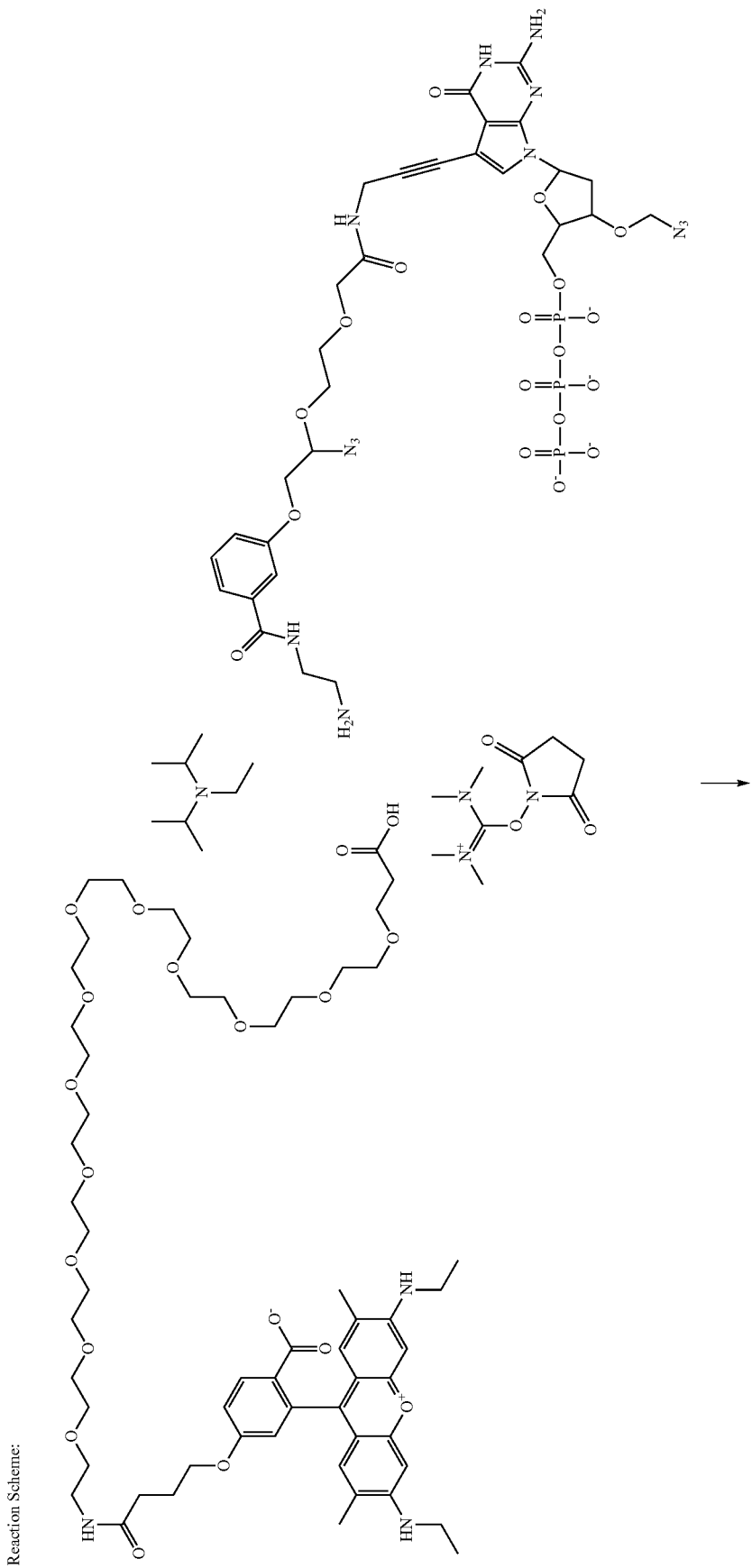
Reaction Scheme:

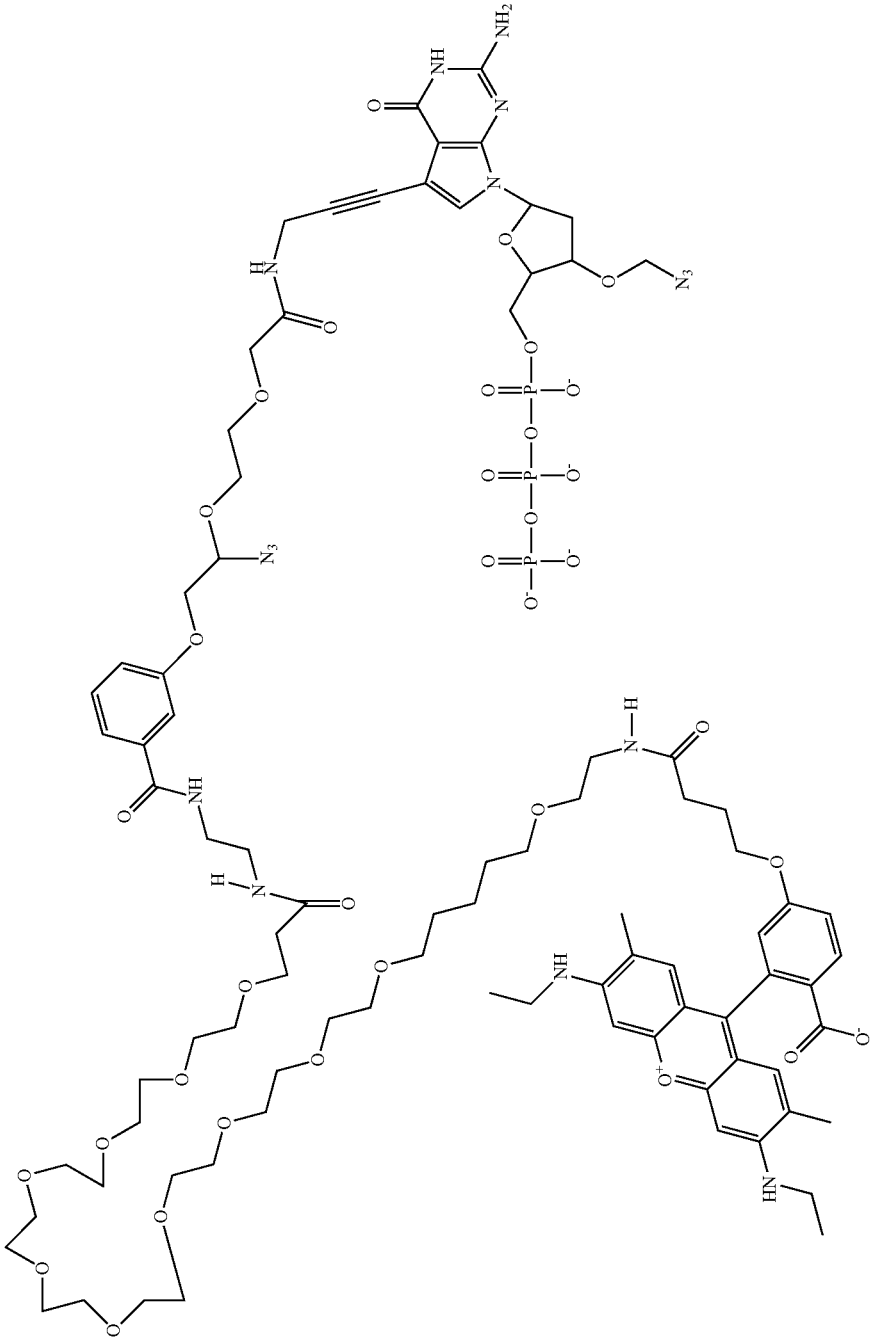

Preparation:

The dye (I-8) was dried after second prep HPLC purification and dissolved in anhydrous DMA (3 mL) and then Hunig's Base (0.036 g) was added. A solution of TSTU (11 mg) in 1 mL of dry DMA was then added. Reaction mixture was stirred at room temperature for 3 h. According TLC (20% $H_2O$ in $CH_3CN$) the activation was completed.

A solution of pppG-LN3 (1.6 mL of stock 35.5 mM) was vac down to dryness. After activation of (I-8) was completed this solution was added to pppG. The reaction was stirred at room temperature under nitrogen atmosphere for 2 h. TLC (20% $H_2O$ in acetonitrile) control indicated the reaction progress. Reaction mixture was kept at −4° C. overnight, 0.1 M TEAB (4 mL) was then added and the mixture was stirred at room temperature for 10 min.

Ion exchange purification: this solution was applied to column with ~20 g of suspension of DEAE sephadex resin in 0.05 M TEAB solution and washed with TEAB from 0.1 M up to 0.35 M.

Coloured fractions eluted at about 0.35 M TEAB were combined, co-evaporated with water to remove more TEAB and vac down to dryness.

Purification: similar to previous compound. Yield: 14 μmol (51%).

Dye (I-11) pppT-I-3

Reaction Scheme:

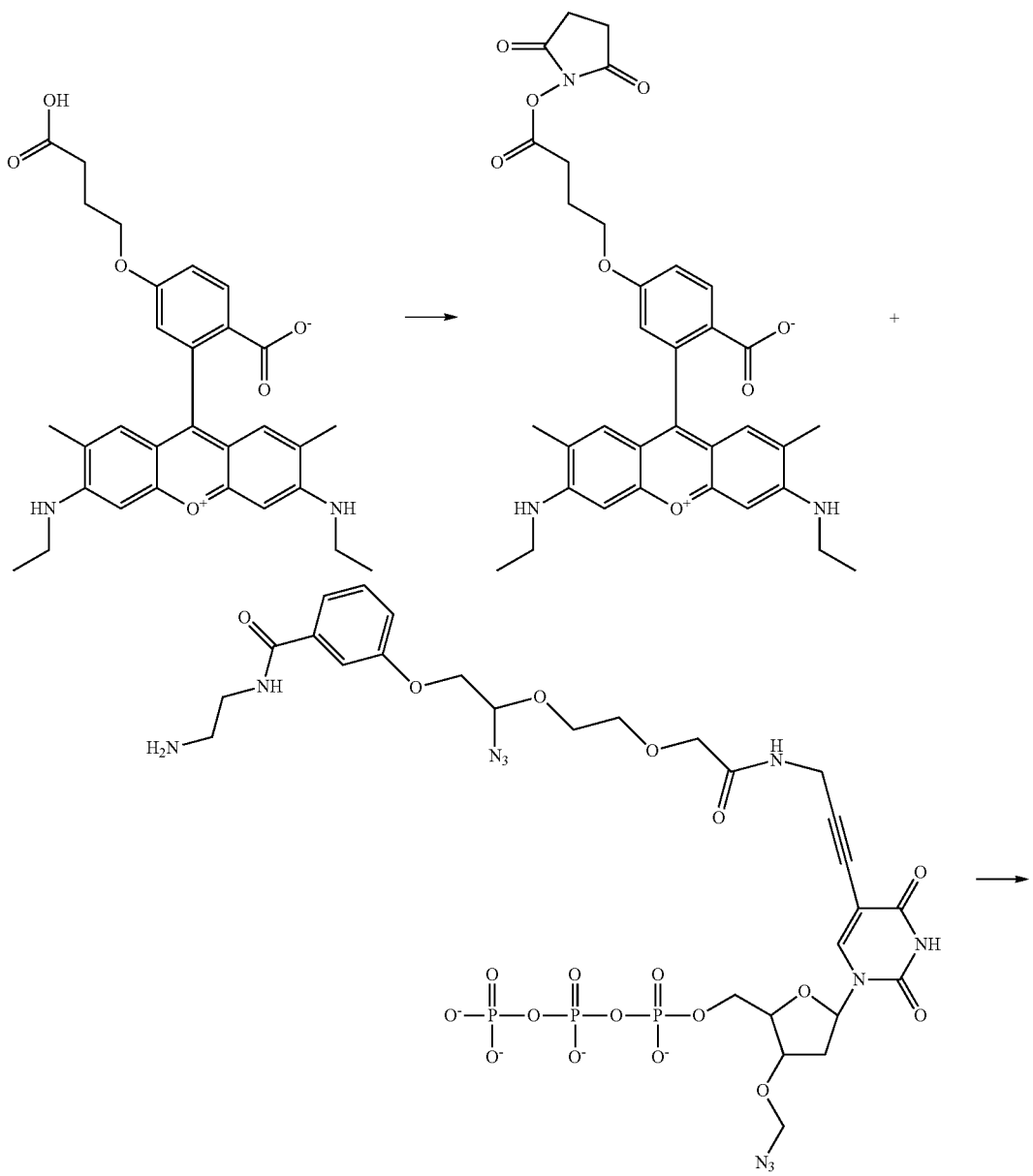

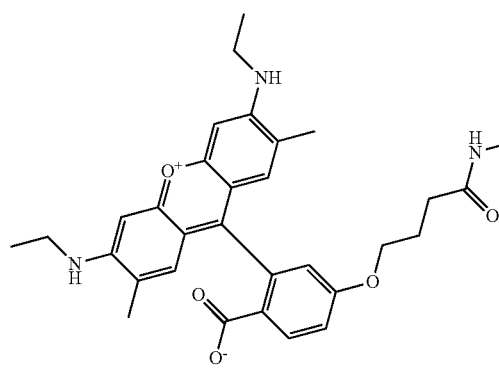
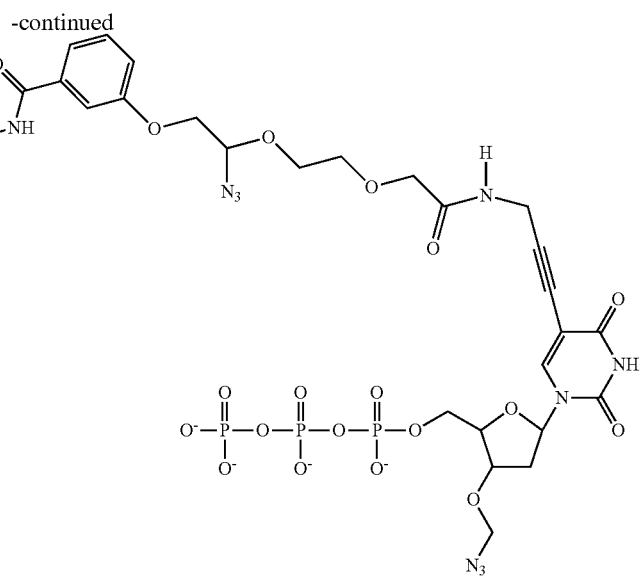

Preparation:

Anhydrous DMA (15 mL) and Hunig's Base (0.06 mL) were added to the dried sample of the dye (I-3) (60 mg). Colourless solution of lactone IC was formed. A solution of TSTU, (0.50 g) in 5 mL of dry DMA was then added to this. The red colour of activated ester (I-6) developed. The reaction mixture was stirred at room temperature for 1 h, According TLC (20% H$_2$O in MeCN) activation completed. After activation was completed this solution was added to the solution of pppT-LN3 (0.23 g) in water (10 mL). The reaction mixture was stirred at room temperature under nitrogen atmosphere for 3 h. Coupling progress was checked by TLC (20% H$_2$O in acetonitrile). Reaction mixture was cooled down to ~4° C. with an ice-bath, then solution of 0.1 M TEAB (5 mL) in water was added and the mixture was stirred at room temperature for 10 min. The reaction mixture was applied to column with ~50 g of DEAE sephadex resin suspension in 0.05 M TEAB solution in water and washed with TEAB (concentration gradient from 0.1 M up to 0.5 M). Coloured fractions were collected and evaporated then co-evaporated again with water to remove more TEAB and vac down to dryness. The residue was then re-dissolve in TEAB 0.1 M. This solution was filtered through a syringe filter 0.2 nm pore size into a corning flask and stored in the freezer. The product was purified by HPLC using C18 reverse phase column with acetonitrile-0.1 M TEAB, the fraction with absorption at 520 nm being collected. Yield 57%.

Dye (I-12)pppT-I-4

Reaction Scheme:

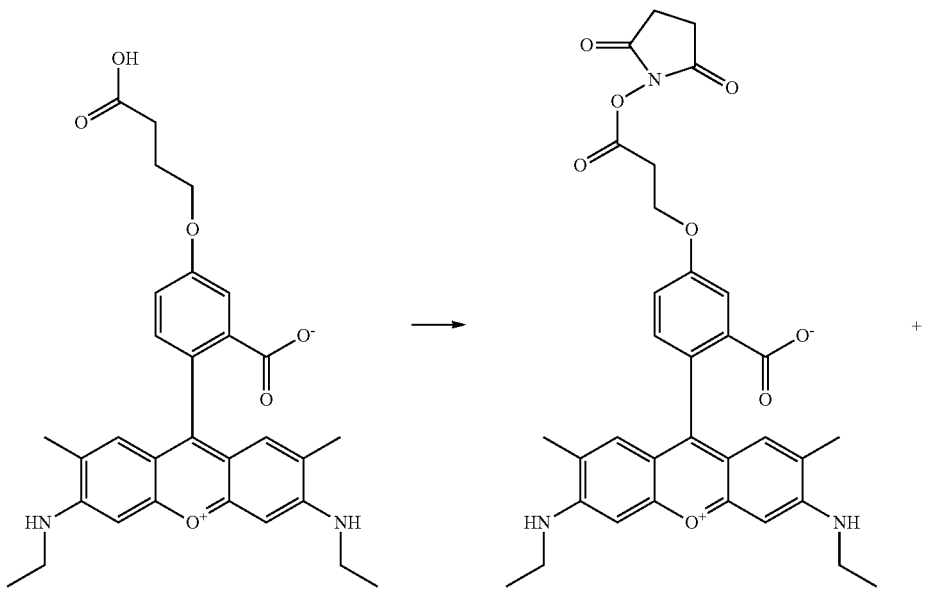

-continued

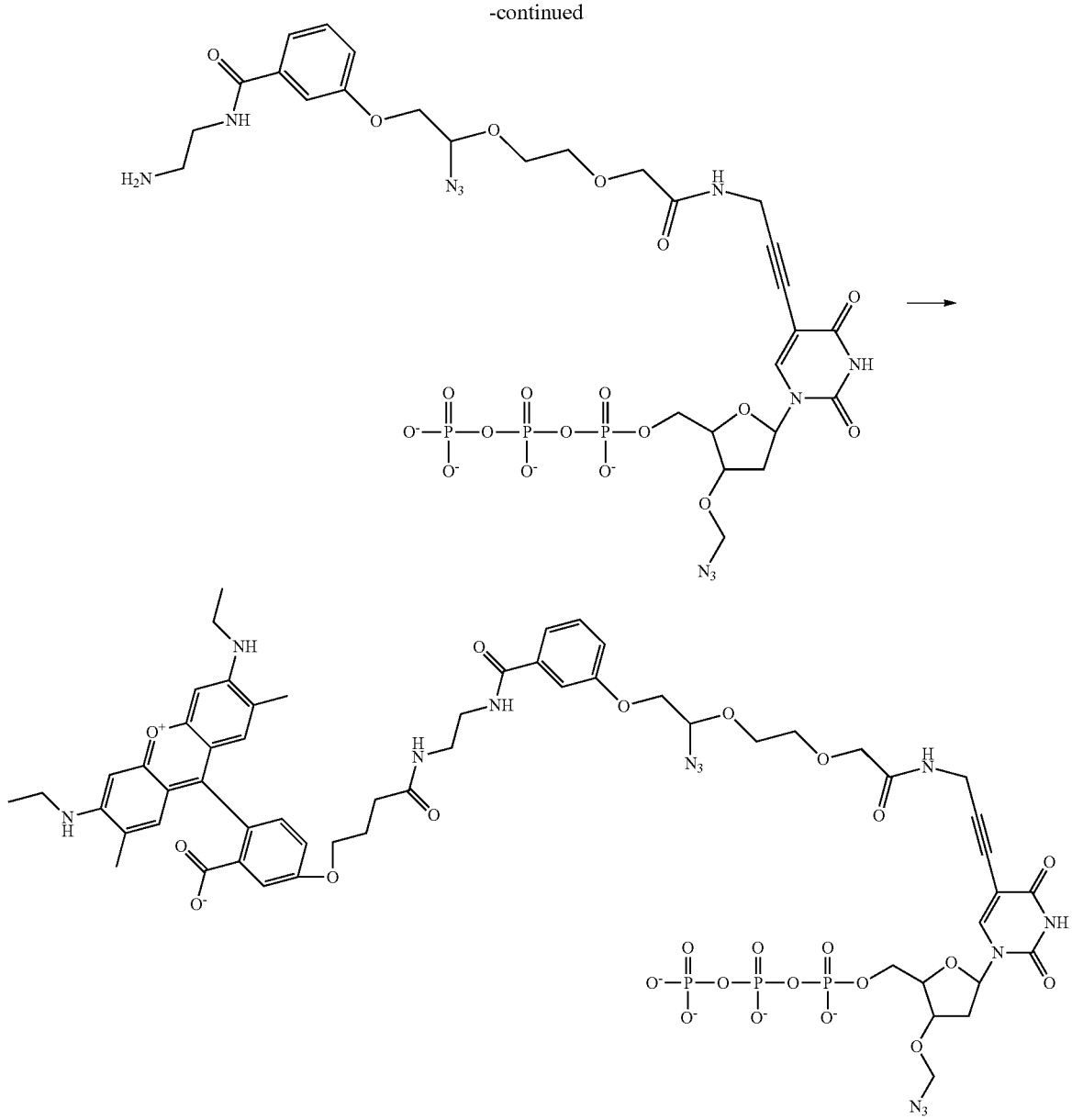

Preparation:

Anhydrous DMA (5 mL) and Hunig's Base (0.02 mL) were added to the dried sample of the dye (I-4) (20 mg). Colourless solution of lactone IC was formed. A solution of TSTU, (0.175 g) in 1 mL of dry DMA was then added to this. Red colour of activated ester (I-6) developed. The reaction mixture was stirred at room temperature for 1 h, According TLC (20% H$_2$O in MeCN) activation completed. After activation was completed this solution was added to the solution of pppT-LN3 (77 mg) in water (3 mL). The reaction mixture was stirred at room temperature under nitrogen atmosphere for 3 h. Coupling progress was checked by TLC (20% H$_2$O in acetonitrile). Reaction mixture was cooled down to −4° C. with an ice-bath, then solution of 0.1 M TEAB (2 mL) in water was added and the mixture was stirred at room temperature for 10 min. The reaction mixture was applied to column with ~20 g of DEAE sephadex resin suspension in 0.05 M TEAB solution in water and washed with TEAB (concentration gradient from 0.1 M up to 0.5 M). Coloured fractions were collected and evaporated then co-evaporated again with water to remove more TEAB and vac down to dryness. The residue was then re-dissolve in TEAB 0.1M. This solution was filtered through a syringe filter 0.2 nm pore size into a corning flask and stored in the freezer. The product was purified by HPLC using C18 reverse phase column with acetonitrile-0.1 M TEAB, the fraction with absorption at 520 nm being collected. Yield 57%.

Dye (I-13) pppT-I-1
Reaction Scheme:
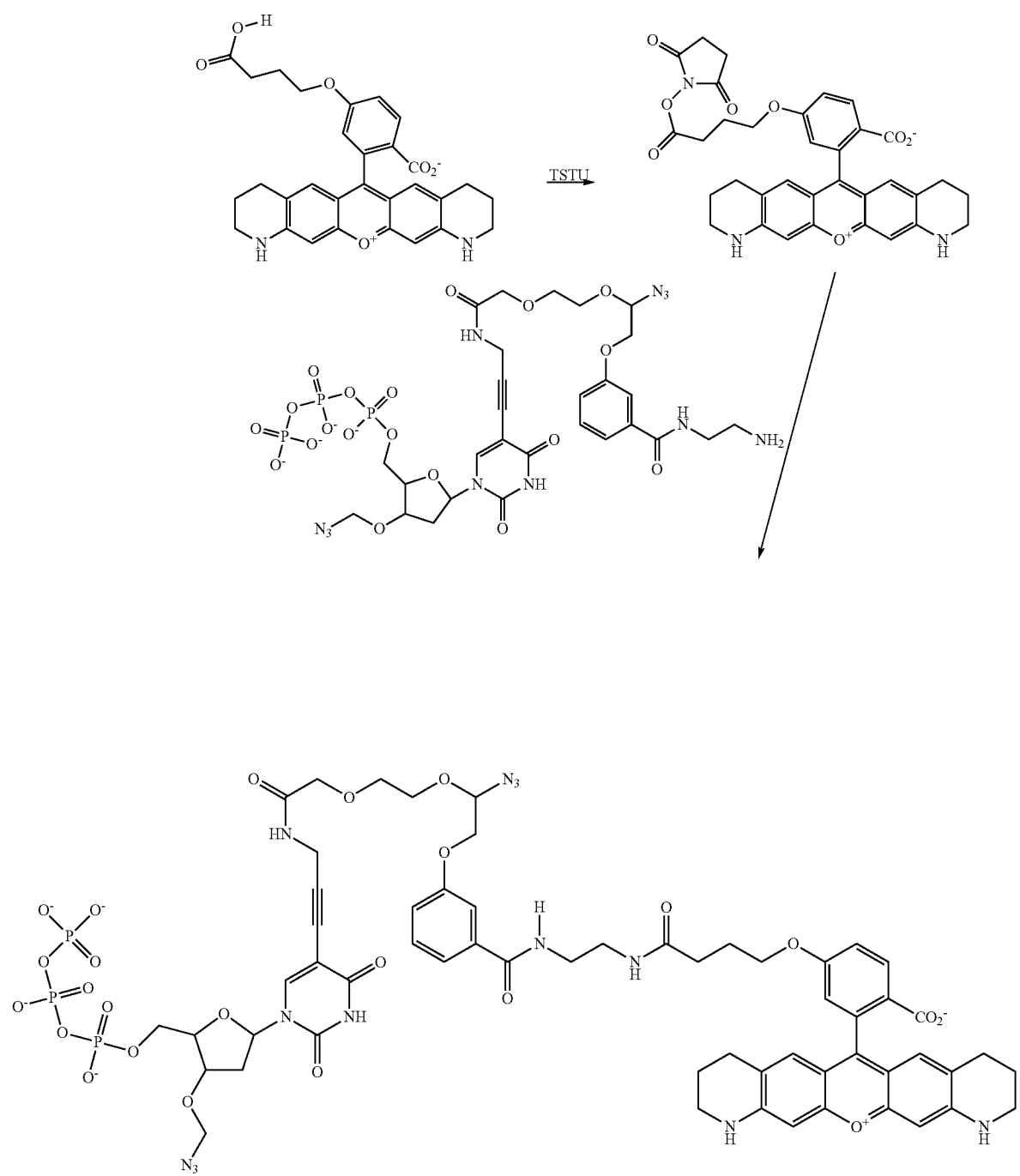

Preparation:

Anhydrous DMA (10 mL) and Hunig's Base (0.04 mL) were added to the dried sample of the dye (I-1) (40 mg). Colourless solution of lactone IC was formed. A solution of TSTU, (0.35 g) in 5 mL of dry DMA was then added to this. Red colour of activated ester developed. The reaction mixture was stirred at room temperature for 1 h. According to TLC (20% H₂O in MeCN), activation was completed. After activation was completed this solution was added to the solution of pppT-LN3 (0.18 g) in water (10 mL). The reaction mixture was stirred at room temperature under nitrogen atmosphere for 3 h. Coupling progress was checked by TLC (20% H₂O in acetonitrile). The reaction mixture was cooled down to ~4° C. with an ice-bath, then a solution of 0.1 M TEAB (5 mL) in water was added and the mixture was stirred at room temperature for 10 min. The reaction mixture was applied to column with ~50 g of DEAE sephadex resin suspension in 0.05 M TEAB solution in water and washed with TEAB (concentration gradient from 0.1 M up to 0.5 M). Coloured fractions were collected and evaporated then co-evaporated again with water to remove more TEAB and vac down to dryness. The residue was then re-dissolved in TEAB 0.1 M. This solution was filtered through a syringe filter 0.2 nm pore size into a corning flask and stored in the freezer. The product was purified by HPLC using C18 reverse phase column with acetonitrile-0.1 M TEAB, fraction with absorption at 535 nm collected. Yield 60%.

Dye (I-14) pppT-I-2

Reaction Scheme:

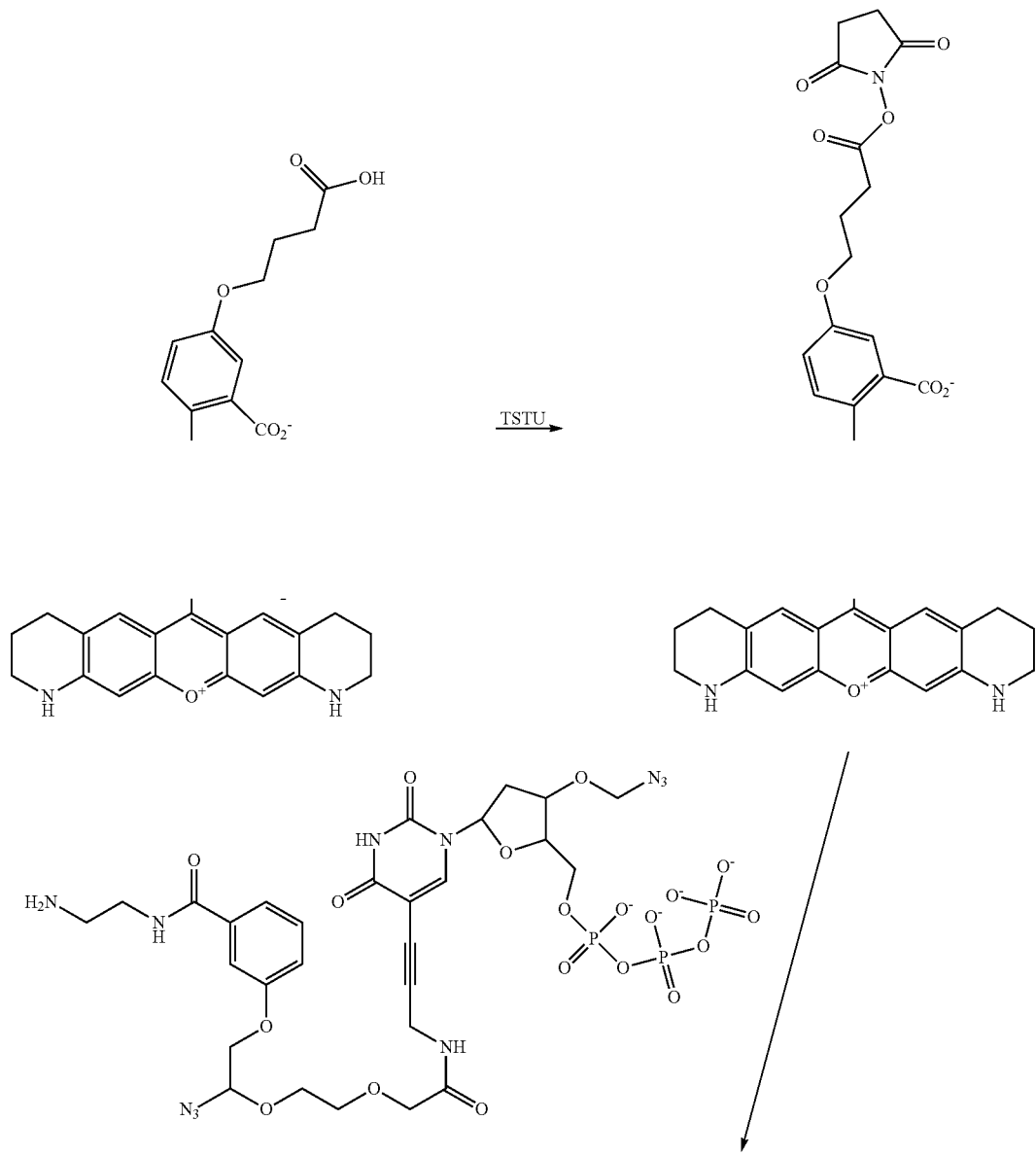

-continued

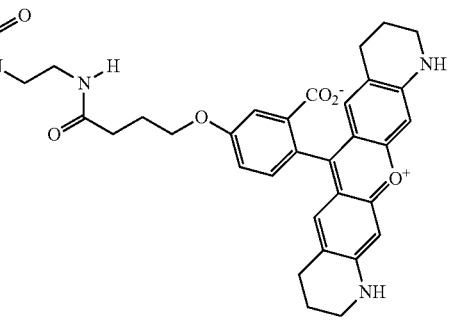

Preparation:

Anhydrous DMA (10 mL) and Hunig's Base (0.04 mL) were added to the dried sample of the dye (I-2) (40 mg). Colourless solution of lactone IC was formed. A solution of TSTU, (0.35 g) in 5 mL of dry DMA was then added to this. Red colour of activated ester developed. The reaction mixture was stirred at room temperature for 1 h. According to TLC (20% $H_2O$ in $CH_3CN$), activation was completed. After activation was completed this solution was added to the solution of pppT-LN3 (0.18 g) in water (10 mL). The reaction mixture was stirred at room temperature under nitrogen atmosphere for 3 h. Coupling reaction progress was monitored by TLC (20% $H_2O$ in acetonitrile). The reaction mixture was cooled down to ~4° C. with an ice-bath, then a solution of 0.1 M TEAB (5 mL) in water was added and the mixture was stirred at room temperature for 10 min. The reaction mixture was applied to column with ~50 g of DEAE sephadex resin suspension in 0.05 M TEAB solution in water and washed with TEAB (concentration gradient from 0.1 M up to 0.5 M). The coloured fractions were collected and evaporated then co-evaporated again with water to remove more TEAB and vac down to dryness. The residue was then re-dissolved in TEAB 0.1 M. This solution was filtered through a syringe filter 0.2 nm pore size into a corning flask and stored in the freezer. The product was purified by HPLC using C18 reverse phase column with acetonitrile-0.1M TEAB, the fraction with absorption at 535 nm being collected. Yield 45%.

Characterisation of New Dyes Vs Known Dyes

Temperature Intensity

Normalized fluorescence intensities of $1.10^{-6}$ M solutions of dyes (I-1) and (I-3) were compared with commercially available dye Atto532 for the same spectral region at different temperature. The intensity of the dyes at 20, 40 and 60° C. were measured. FIG. 1 shows the relative intensity of the dyes at each temperature. The commercial dye Atto532 shows a greater loss of fluorescence intensity at higher temperatures relative to the I-1 and I-3 dyes. FIG. 1 demonstrates that the fluorescence of the new dyes in water based solutions is less variable with the temperature.

Intensity when Conjugated to Nucleotides

Normalised Fluorescence spectra of $1.10^{-6}$ M solutions of dye-nucleobase conjugates (I-13)-T and (I-11)-T were compared with structural analogue when pppT is conjugated with commercially available dye Atto532.

Figure 2:
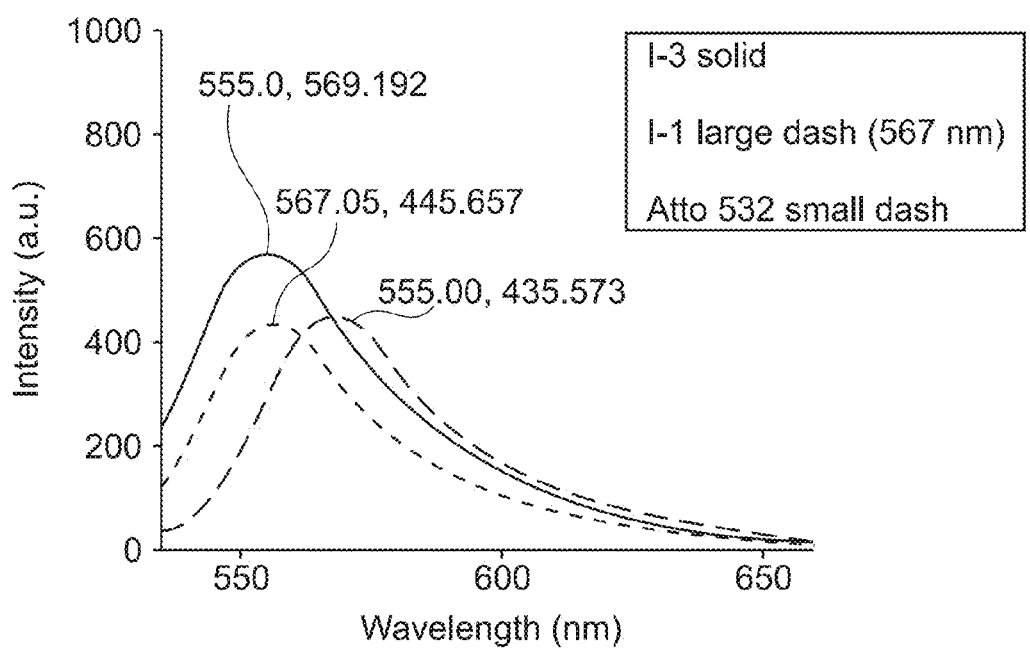
FIG. 2 demonstrates that fluorescence of the nucleobase conjugates based on these new dyes in water based solutions is higher than commercially available dyes when excited by 532 nm light. Normalised Fluorescence spectra of $1.10^{-6}$ M solutions of dye-nucleobase conjugates (I-13)-T and (I-11)-T were compared with structural analogue when pppT is conjugated with commercially available dye Atto532. The 1-3 dye is brighter than the atto 532 dye at the same nucleotide concentration. The I-1 dye is red shifted compared to the atto 532 dye.

FIG. 2 demonstrates that fluorescence of the nucleobase conjugates based on these new dyes in water based solutions higher than commercially available dyes when excited by 532 nm light. The 1-3 dye is brighter than the atto 532 dye at the same nucleotide concentration. The I-1 dye is red shifted compared to the atto 532 dye.

Figure 3:
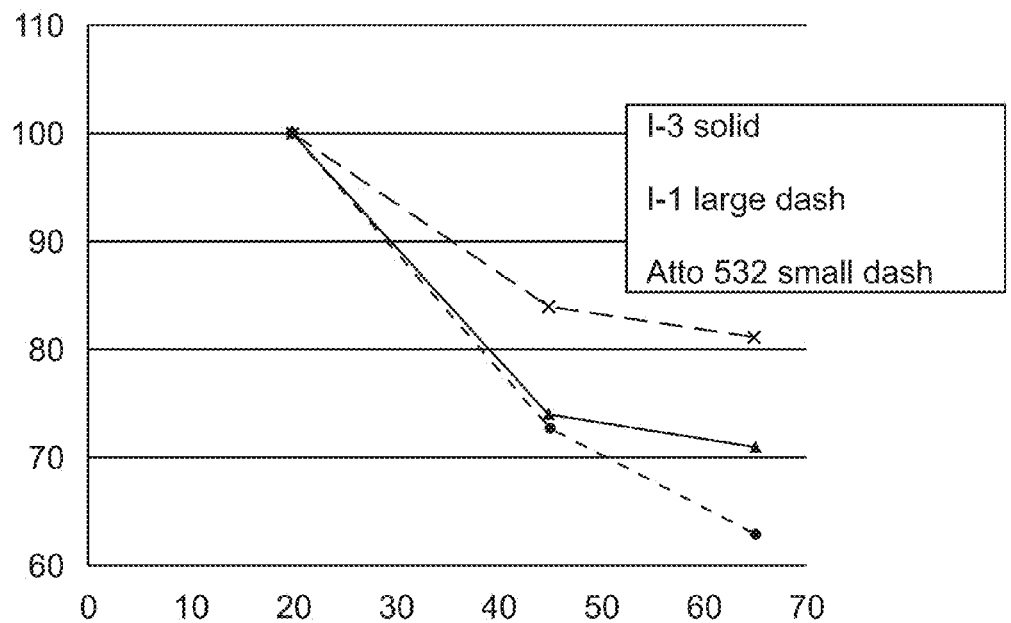
FIG. 3 demonstrates that fluorescence of new dyes in water based solutions is less dependable on temperature. Normalized fluorescence intensities $1.10^{-6}$ M solutions of dyes when conjugated with nucleobase, T-(I-11) and T-(I-13) as compared with commercially available dye Atto532 conjugated with the same T-nucleobase. Both the I-1 and I-3 dyes show a higher fluorescence intensity at elevated temperatures compared to atto-532.

FIG. 3 demonstrates that fluorescence of new dyes in water based solutions is less dependable on temperature. Normalized fluorescence intensities $1.10^{-6}$ M solutions of dyes when conjugated with nucleobase, T-(I-11) and T-(I-13) as compared with commercially available dye Atto532 conjugated with the same T-nucleobase. Both the I-1 and 1-3 dyes show a higher fluorescence intensity at elevated temperatures compared to atto-532.

Sequencing Data

Figure 4:
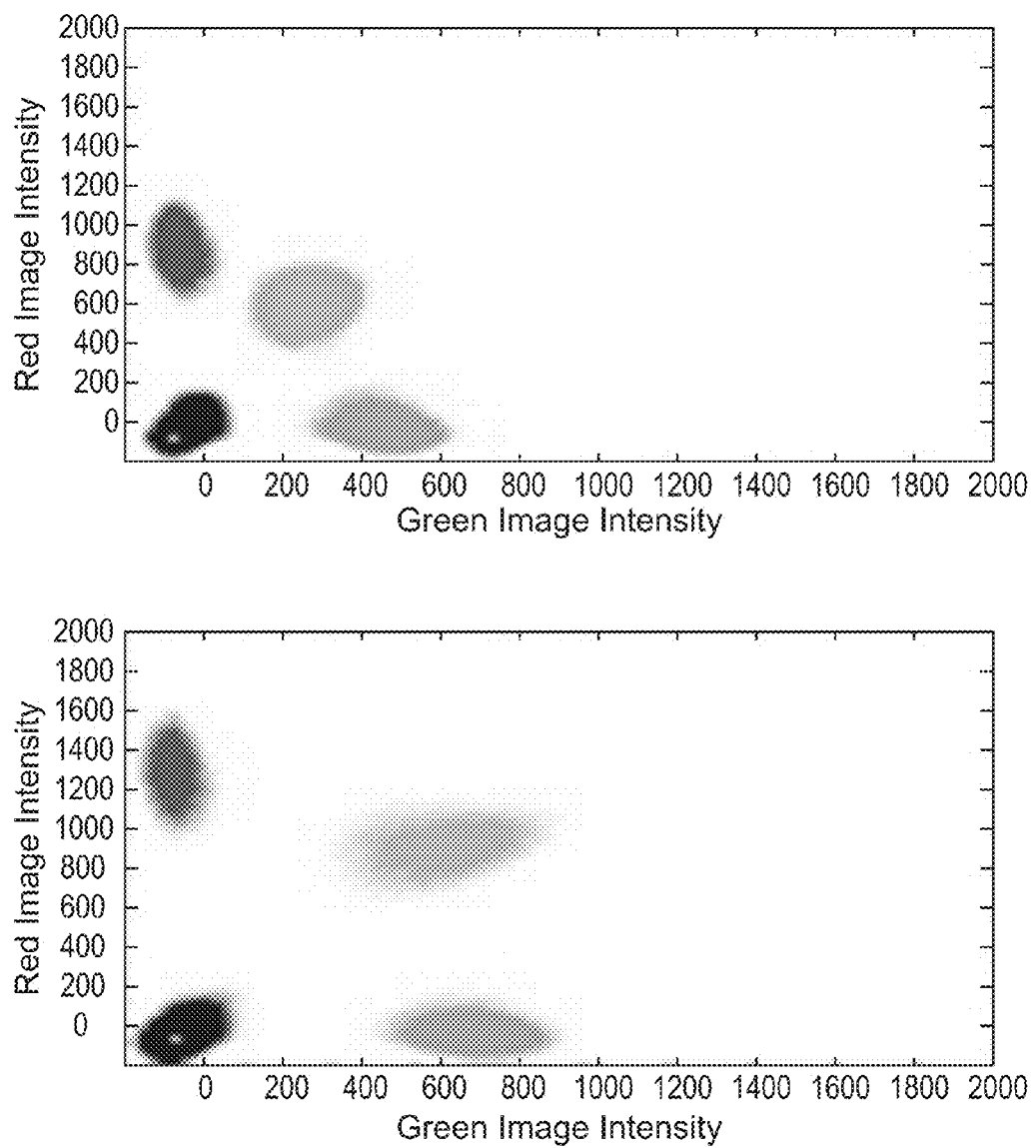
FIG. 4 demonstrates better distinguishing of fluorescence signals when a nucleobase been labelled with the new dye in according with the invention (I-3) (lane 6) as compared with standard fluorophore set when the same nucleobase been conjugated with commercially available dye Atto532 (control 1).

FIG. 4 demonstrates better distinguishing of fluorescence signals when a nucleobase been labelled with the new dye in according with the invention (I-3) (lane 6) as compared with standard fluorophore set when the same nucleobase been conjugated with commercially available dye Atto532 (control 1). FIG. 4 shows a plot of red intensity vs green intensity in an Illumina 4 colour sequencing run. The higher distance between the groups of dyes signals lowers the chances of a miss-call, and therefore increases the accuracy of sequencing. The increase in brightness of the 1-3 dye compared to the commercial dye means the sequencing data is improved.

The invention claimed is:
1. A compound of formula (I) and mesomers thereof:

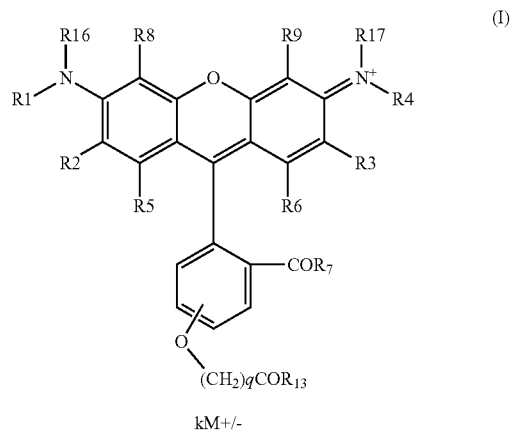

Wherein $M^{+/-}$ is a common counter ion,
k is an integer of from 0 to 6,
q is an integer of from 1 to 6, $R_1$ is H or an alkyl, aryl or substituted alkyl or substituted aryl group, $R_2$ is H, alkyl or substituted alkyl group, halogen, carboxy, carboxamide, hydroxy- or alkoxy group, or $R_2$ together with $R_1$ or $R_5$ is a carbon or heterosubstituted chain forming a ring, $R_3$ is H, alkyl or substituted alkyl group, halogen, carboxy, carboxamide, hydroxy- or alkoxy group or $R_3$ together with $R_4$ or $R_6$ is a carbon or heterosubstituted chain forming a ring, $R_4$ is H or an alkyl, aryl or substituted alkyl or substituted aryl group, $R_5$ and $R_6$ are H, alkyl or substituted alkyl group, halogen, hydroxy- or alkoxy group, $R_8$ is H, halogen, hydroxy- or alkoxy group, alkyl or substituted alkyl group or together with $R_1$ is a carbon or heterosubstituted carbon chain forming a ring, $R_9$ is H, halogen, hydroxy- or alkoxy group, alkyl or substituted alkyl group or together with $R_4$ is a carbon or heterosubstituted carbon chain forming a ring, $R_7$ is $OR_{11}$ or $NR_{11}R_{12}$ where $R_{11}$ and $R_{12}$ are independently H, alkyl or a substituted alkyl, $R_{13}$ is $OR_{14}$ or $NR_{14}R_{15}$ where $R_{14}$ and $R_{15}$ are independently H, alkyl or a substituted alkyl; aryl or a substituted aryl, and $R_{16}$ and $R_{17}$ are independently H or an alkyl, aryl or substituted alkyl or substituted aryl group.

2. The compound of claim 1 wherein $R_{16}$ is alkyl and $R_{17}$ is alkyl.

3. The compound of claim 1 wherein $R_1$, $R_4$, $R_5$, $R_6$, $R_8$ and $R_9$ are all H, $R_2$ and $R_3$ are H or $CH_3$.

4. The compound of claim 1 wherein $R_{16}$ and $R_{17}$ are H.

5. The compound of claim 1 wherein $R_1$ is linked to $R_2$ or $R_8$ via a chain of $CH_2$ groups to form a ring, and $R_4$ is linked to $R_3$ or $R_9$ via a chain of $CH_2$ groups to form a ring.

6. The compound of claim 5 wherein $R_1$ and $R_2$ form a six membered ring, $R_3$ and $R_4$ form a six membered ring, $R_5$, $R_6$, $R_8$ and $R_9$ are H.

7. The compound of claim 1 wherein one or more of $R_1$, $R_4$, $R_{16}$ and $R_{17}$ are alkyl groups substituted with an $SO_3^-$ group.

8. The compound of claim 1 wherein $R_7$ is OH.

9. The compound of claim 1 wherein q is 3.

10. The compound of claim 1 wherein $R_{13}$ is OH.

11. The compound of claim 1 wherein $R_{13}$ is $NR_{14}R_{15}$ where $R_{14}$ is H or alkyl and $R_{15}$ is alkyl or a substituted alkyl.

12. The compound of claim 11 wherein the compound is attached to a nucleotide or oligonucleotide via substituted alkyl group $R_{15}$.

* * * * *